US006570034B2

(12) United States Patent
Szajewski et al.

(10) Patent No.: US 6,570,034 B2
(45) Date of Patent: May 27, 2003

(54) BLOCKED PHENYLENEDIAMINE DEVELOPERS FOR A COLOR PHOTOGRAPHIC ELEMENT

(75) Inventors: Richard P. Szajewski, Rochester, NY (US); Lyn M. Irving, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 11 days.

(21) Appl. No.: 09/871,522

(22) Filed: May 31, 2001

(65) Prior Publication Data

US 2002/0012886 A1 Jan. 31, 2002

Related U.S. Application Data

(60) Provisional application No. 60/211,299, filed on Jun. 13, 2000.

(51) Int. Cl.[7] .............................................. C07C 261/00

(52) U.S. Cl. ............................. 560/25; 560/33; 560/29; 560/30; 564/42; 548/309.7; 546/300

(58) Field of Search ......................... 548/309.7; 560/25, 560/33, 29, 30; 564/42; 546/300

(56) References Cited

U.S. PATENT DOCUMENTS 6,197,722 B1 3/2001 Irving et al.

OTHER PUBLICATIONS

Correlation of Some Physical and Chemical Properties of Substituted p–Phenylenediamines and Their Dye Derivatives, by R. L. Bent et al., in Photographic Science and Engineering, vol. 8, No. 3, May–Jun. 1964, pp. 125–137.

*Primary Examiner*—Samuel Barts
(74) *Attorney, Agent, or Firm*—Chris P. Konkol

(57) ABSTRACT

The present invention relates to a novel blocked phenylenediamine developer useful, in reactive association, for enabling, on development, a non-magenta color, for example a cyan color, from a dye-forming coupler. In one embodiment, the developer has the property that the dye color formed with the coupler is distinctly different from the color formed by the same coupler with an oxidized form of the conventional developer 4-(N-ethyl-N-2-hydroxyethyl)-2-methylphenylenediamine. The invention is also directed to a light-sensitive silver-halide color photographic element comprising the blocked developing agent according to the present invention.

6 Claims, No Drawings

BLOCKED PHENYLENEDIAMINE DEVELOPERS FOR A COLOR PHOTOGRAPHIC ELEMENT

This application claims the benefit of Provisional Application Ser. No. 60,211,299 filed Jun. 13, 2000.

FIELD OF THE INVENTION

The present invention is directed to novel blocked color developers for photographic imaging element. In particular, the blocked developer is a phenylenediamine developing agent that can be incorporated into the imaging element to produce a distinct color.

BACKGROUND OF THE INVENTION

Japanese kokai JP 10090854 (1996) teaches different developers in the same color unit layer (having spectral sensitivity in the same wavelength range) in a photothermographic imaging element, in order to obtain better image or tone gradation.

U.S. Pat. No. 6,197,722 B1 to Irving et al. teaches a method of imaging, useful comprising providing an imaging member having at least one light insensitive layer comprising a catalytic center and multifunctional dye forming coupler, imagewise applying distinct developer solutions that will react with the multifunctional dye forming coupler to produce dyes of different colors. A preferred method of imagewise application of developer solution is by the technique known as “inkjet.”

R. L. Bent et al., in *Photographic Science and Engineering*, Vol. 8, No. 3, May–June 1964 disclosed that the frequencies of maximum absorption of various dyes derived from p-phenylenediamines are closely related to the half-wave oxidation potentials of the compounds. As one point on various plotted correleations, experimental Compound A is disclosed (in Table II), in a 4-amino-N,N-dialkylaniline structure has 3,5-di-$CH_3$ substitution. The compounds are not disclosed as having any commercial utility and the reference might be construed as teaching that the use of Compound A would not be useful, since it would not provide the desired magenta hue with a conventional magenta coupler.

PROBLEM TO BE SOLVED BY THE PRESENT INVENTION

Light-sensitive imaging elements which form yellow, magenta and cyan dye records of comparable density-forming ability and consistent stability in all three color records using conventional developers can be difficult. Cyan and yellow dye records can be a problem in this regard, especially in photothermographic elements. Accordingly, alternative ways of forming cyan or yellow dyes are especially useful in such imaging elements.

Another problem with conventional cyan dye-forming couplers relates to the fact that the raw stock stability of photographic elements is influenced by the physical properties of materials employed to formulate that element. Cyan dye-forming couplers are particularly prone to crystallization on extended cold keeping. This crystallization both degrades the image-forming ability of such an element and mars the appearance of images produced in such an element. This problem can be particularly acute in photothermographic or heat developable elements since it may be desirable to keep these elements cold before use, in order to prevent premature reaction.

SUMMARY OF THE INVENTION

The present invention relates to a novel blocked phenylenediamine developer useful, in reactive association, for enabling, on development, a non-magenta color, for example a cyan color, from a dye-forming coupler.

In one embodiment, the developer has the property that the dye color formed with the coupler is distinctly different from the color formed by the same coupler with an oxidized form of the conventional developer 4-(N-ethyl-N-2-hydroxyethyl)-2-methylphenylenediamine. In one embodiment, the developer has the property that it is capable of forming a distinctly colored cyan dye with one coupler, while the same coupler forms a magenta dye with an oxidized form of the conventional developer 4-(N-ethyl-N-2-hydroxyethyl)-2-methylphenylenediamine. The latter developer (also known as “CD2”), which developer is widely used, is used herein as a standard means for the purpose of enabling a convenient color comparison, but other developers could have been substituted instead.

In a first embodiment, a light-sensitive silver-halide color photographic element has a red-light-sensitive silver-halide layer unit and a first blocked coupling developer, a green-light-sensitive silver-halide layer unit and a second blocked coupling developer, and a blue-light-sensitive silver-halide layer unit having a third blocked coupling developer, wherein at least two of the first, second, and third blocked coupling developers are different and wherein at least one layer unit, or imaging layer in the layer unit, has a blocked developer according to the present invention.

DETAILED DESCRIPTION OF THE INVENTION

As mentioned above, the invention relates to novel blocked developer that can be used in a light-sensitive color photographic imaging element comprising at least one chromogenic coupler in reactive association with the blocked developer. In one embodiment, the blocked developer liberates a developing agent enabling cyan color from the coupler on development, wherein the same coupler forms at least one other distinctly colored dye with an oxidized form of the conventional developer 4-(N-ethyl-N-2-hydroxyethyl)-2-methylphenylenediamine. The blocked developer (or “developer precursor”) liberates a phenylenediamine type of developer as described in more detail below.

Thus, the developer according to the present invention can have a number of possible uses, including use in imaging elements having a number of different couplers and a number of different developing agents. There can be two different couplers or three different couplers in the imaging element. It is possible to have more than three couplers, per the Japanese kokai mentioned above. It is also possible to have more than three different developers (or blocked developers), three different developers (or blocked developers), two different developers (or blocked developers), or a single developer (or blocked developer). In one embodiment, there are two different developers and three different couplers, which may minimize costs by not having more than two developers.

Thus, the developer can be employed in an imaging element comprising, for example, a red-light-sensitive layer unit, a green-light-sensitive layer unit and a blue-light-sensitive layer unit, wherein at least one layer in at least two different layer units has in reactive association an independently selected dye forming coupler and an independently selected blocked developer. Preferably, the blocked developer is different in two layer units. Alternatively, the imaging element can comprise a red-light-sensitive layer unit, a green-light-sensitive layer unit and a blue-light-sensitive layer unit, wherein all three layer units have in reactive association an independently selected dye forming coupler and an independently selected blocked developer, wherein the dye coupler is different in each layer unit and the developing agent is the same in two layer units. As a further alternative, the element can comprises a red-light-sensitive layer unit, a green-light-sensitive layer unit and a blue-light-sensitive layer unit, wherein all three layer units have in reactive association an independently selected dye-forming coupler and an independently selected blocked developer, wherein the dye couplers are the same in only two of the layer units and wherein the blocked developer is different in said two layer units. Alternatively, the element can comprise a red-light-sensitive layer unit, a green-light-sensitive layer unit and a blue-light-sensitive layer unit, wherein two layer units have in reactive association a common dye-forming coupler, wherein the third layer unit has a distinct coupler, and wherein the blocked developer is the same in two of the layer units.

In a preferred variant, the element is a photothermographic element. In this embodiment, an imagewise exposed element is developed by heat treatment. In another variant of the first embodiment, an imagewise exposed element is developed by treatment with base either by contacting the element to a pH controlling solution or by contacting the element to a pH controlling laminate.

When the formed image is intended for human viewing, a first blocked coupling developer is cyan dye forming, a second blocked coupling developer is magenta dye forming, and a third blocked coupling developer is yellow dye forming. Preferably, developer of the present invention is present, in reactive association with a coupler, in the red light sensitive color layer unit. However, if the formed image is to be scanned, it is possible to produce other colored dyes.

The term "developer precursor" includes "blocked developer" and other compounds that convert or otherwise react to form a developing agent. The developer precursors are preferably supplied in a blocked form as described below and elsewhere. These developer precursors can release any developers known in the art which are coupling developers and enable the formation of distinctly colored dyes from the same coupler. By "distinctly colored" is meant that the dyes formed differ in the wavelength of maximum adsorption by at least 50 nm. It is preferred that these dyes differ in the maximum adsorption wavelength by at least 65 nm and more preferred that they differ in the maximum adsorption wavelength by at least 80 nm. It is further preferred that at least a cyan, a magenta, and a yellow dye are formed. Preferably a cyan dye-forming developer, a magenta dye-forming developer and a yellow dye-forming developer are employed to form respectively cyan, magenta and yellow dyes from the same coupler. In another embodiment, a black dye forming developer is additionally employed. In yet another embodiment multiple cyan dye forming, magenta dye forming and yellow dye forming developers can be individually employed to form a greater gamut of colors or to form colors at greater bit depth.

Typically, a cyan dye is a dye having a maximum absorption at between 580 and 720 nm, with preferably a maximum absorption between 590 and 680 nm, more preferably a peak absorption between 600 and 670 nm and most preferably a peak absorption between 605 and 655 nm. Typically, a magenta dye is a dye having a maximum absorption at between 500 and 580 nm, with preferably a maximum absorption between 515 and 565 nm, more preferably a peak absorption between 520 and 560 nm and most preferably a peak absorption between 525 and 555 nm. Typically, a yellow dye is a dye having a maximum absorption at between 400 and 500 nm, with preferably a maximum absorption between 410 and 480 nm, more preferably a peak absorption between 435 and 465 nm and most preferably a peak absorption between 445 and 455 nm. The concentrations and amounts of the distinct developers and the dye-forming coupler will typically be chosen so as to enable the formation of dyes having a density at maximum absorption of at least 0.7, preferably a density of at least 1.0, more preferably a density of at least 1.3 and most preferably a density of at least 1.6. For cyan, magenta or yellow dyes, these will be densities measured in a photographic element using status M filters. Further, the dyes will typically have a half height band width (HHBW) of between 70 and 170 nm in the region between 400 and 700 nm. Preferably, the HHBW will be less than 150 nm, more preferably less than 130 nm and most preferably less than 115 nm. Additional details of preferred dye hues for images intended for direct viewing are described by McInerney et al in U.S. Pat. Nos. 5,679,139, 5,679,140, 5,679,141 and 5,679,142, the disclosures of which are incorporated by reference.

The blocked developer according to the present invention enables the formation of a cyan colored dye when the oxidized form of the released developer reacts with the coupler A-5 (defined above), wherein developer is a compound selected from the class of compounds represented by the following structure:

$$A—(CR^1{=\!=}CR^2)_n—NHY \qquad (I)$$

wherein:

n is 0, 1 or 2;

A is OH, or $NR^3R^4$;

Y is H, or a group that cleaves before or during a coupling reaction to form YH; and $R^1$ $R^2$, $R^3$ and $R^4$, which can be the same or different are individually H, alkyl, substituted alkyl, alkenyl, substituted alkenyl, aryl, substituted aryl, halogen, cyano, alkoxy, substituted alkoxy, aryloxy, substituted aryloxy, amino, substituted amino, alkylcarbonamido, substituted alkylcarbonamido, arylcarbonamido, substituted arylcarbonamido, alkylsulfonamido, arylsulfonamido, substituted alkylsulfonamido, substituted arylsulfonamido, or sulfamyl or wherein at least two of $R^1$ $R^2$, $R^3$ and $R^4$ together can further form a substituted or unsubstituted carbocyclic or heterocyclic ring structure. Preferably, $(CR^1{=\!=}CR^2)_n$ forms an aromatic ring, more preferably a phenylene ring that can further be substituted or unsubstituted.

In one preferred embodiment, in Structures I, the partial structure $—(CR^1{=\!=}CR^2)_n—$ represents a substituted or unsubstituted phenylene moiety. When $—(CR^1{=\!=}CR^2)_n—$ represents an aromatic moiety, the moieties —A and —NHY are preferably in a para relationship, one to another.

In Structure I, when Y is a group that cleaves before or during a coupling reaction to form YH, then Y is preferably the moiety $Q—R^6$ wherein:

$R^6$ is H, alkyl substituted alkyl, alkenyl, substituted alkenyl, alkynyl, substituted alkynyl, aryl, substituted aryl, heterocyclic or substituted heterocyclic, and Q is $—SO_2—$, $—SO—$, $—SO_3—$, —CO—, —COCO—, —CO—O—, —CO(NR7)—, —COCO—O, $—OCO—N(R^7)—$ or $—SO_2—N(R^7)—$, where $R^7$ is H or the groups described in $R^6$.

In the developer structures described herein, the word "substituted" at each occurrence represents any group other than H needed to satisfy the required valence where the group does not adversely affect the required properties. The word "substituted" preferably represents one or more of a linear or branched carbonaceous group which can be cyclic or acyclic, a heterocyclic group, an aromatic carbonaceous group, an arylalkyl group, a halogen atom, a cyano group, a nitro group, a ureido group, an ether group, an ester group, an amine group, an amide group, a thioether group, a thioester group, a sulfonyl group or a sulfamyl group.

Preferably, the imaging element comprises a blocked form of a developer that results in a cyan dye being formed when the oxidized form of the developer is reacted with the coupler of the present invention. Preferably, the developer is the neutral or photographically acceptable salt form of the compound represented by the following Structure II:

II

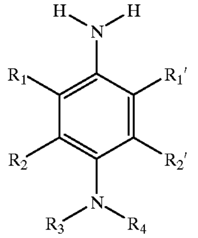

$R_1$, $R_1'$, $R_2$, $R_2'$, $R_3$ and $R_4$ which can be the same or different are individually H, alkyl, substituted alkyl, alkenyl, substituted alkenyl, aryl, substituted aryl, halogen, cyano, hydroxy, alkoxy, substituted alkoxy, aryloxy, substituted aryloxy, amino, substituted amino, alkylcarbonamido, substituted alkylcarbonamido, arylcarbonamido, substituted arylcarbonamido, alkylsulfonamido, arylsulfonamido, substituted alkylsulfonamido, substituted arylsulfonamido, or sulfamyl or wherein at least two of $R_1$, $R_1'$, $R_2$, $R_2'$, $R_3$ and $R_4$ together further form a substituted or unsubstituted carbocyclic or heterocyclic ring structure; except that neither $R_1$ nor $R_1'$ can be H. Preferably, the substituents on $R_1$ and $R_1'$ have at least one carbon or halogen atom.

Preferably, $R_1$ and $R_1'$ is independently a substituted or unsubstituted alkyl or alkoxy or an alkylsulfonamido, more preferably a C1 to C4 alkyl or alkoxy, most preferably, the alkyl is an n-alkyl substituent. Preferably, $R_2$ and $R_2'$ are hydrogen. Preferably, $R^3$ and $R^4$ are independently hydrogen or a substituted or unsubstituted alkyl group or $R^3$ and $R^4$ are connected to form a ring;

More preferably, the developer is the neutral or photographically acceptable salt form of the compound represented by the following Structure III:

III

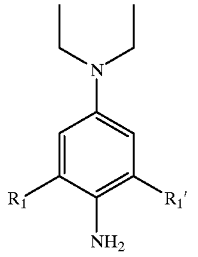

Wherein $R_1$ and $R_1$ are as described above.

Some specific examples of developers according to the present invention include, but are not limited to, the oxidized form of a color developer chosen from the group consisting of 4-N,N-diethyl-2-methyl-6-methoxyphenylenediamine, 4-N,N-diethyl-2,6-dimethylphenylenediamine, 4-(N-ethyl-N-2-methanesulfonylaminoethyl)-2,6-dimethylphenylenediamine, 4-(N-ethyl-N-2-hydroxyethyl)-2,6-dimethylphenylenediamine, 4-N,N-diethyl-2-methanesulfonylaminoethyl-6-methylphenylenediamine, 4-(N-ethyl-N-2-hydroxyethyl)-2-ethoxyphenylenediamine, and 4-(N-ethyl-N-2-methoxyethyl)-2,6-dimethylphenylenediamine. As evidenced by 4-(N-ethyl-N-2-hydroxyethyl)-2-ethoxyphenylenediamine, in which the ethoxy substituent apparently causes sufficient shifting of the $E_{1/2}$ of the developer to allow the desired hue shift on coupling, ortho, ortho substitution is not always required.

Preferred cyan dye forming developers can also be characterized in having an $E_{1/2}$ at pH 11 less positive than 200 mV. The sign convention and method of measuring the oxidation-reduction potential or E ½ of a developer is that described in *The Theory of the Photographic Process,* 4th ed., T. H. James, ed., Macmillan, New York 1977 at pages 291 through 403, the disclosures of which are incorporated by reference.

A specific example of a developing agent useful in the present invention, in neutral or salt form, is represented by the following Structure IV:

IV

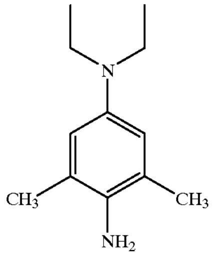

Preferably, at least one other color unit layer, more preferably two other color unit layers, contains a second developer which is also a phenylene diamine developer that, however, differs from that of the above structures II through IV.

Some specific examples of such other developers include, but are not limited, to N,N-diethyl-p-phenylenediamine, 4-N,N-diethyl-2-methylphenylenediamine, 4-(N-ethyl-N-2-methanesulfonylaminoethyl)-2-methylphenylenediamine, 4-(N-ethyl-N-2-hydroxyethyl)-2-methylphenylenediamine, 4-N,N-diethyl-2-methanesulfonylaminoethylphenylenediamine, 4-(N-ethyl-N-2-methoxyethyl)-2-methylphenylenediamine, 4,5-dicyano-2-isopropylsulfonylhydrazinobenzene and 4-amino-2,6-dichlorophenol. *The Theory of the Photographic Process,* 4th ed., T. H. James, ed., Macmillan, New York 1977 at pages 291 through 403, the disclosures of which are incorporated by reference, discloses some specific developers useful in the practice of this invention. Other useful developers and developer precursors are disclosed by Hunig et al, *Angew. Chem.,* 70, page 215-ff (1958), by Schmidt et al, U.S. Pat. No. 2,424,256, Pelz et al, U.S. Pat. No. 2,895,825, Wahl et al, U.S. Pat. No. 2,892,714, Clarke et al, U.S. Pat. Nos. 5,284,739 and 5,415,981, Takeuchi et al, U.S. Pat. No. 5,667,945, and Nabeta U.S. Pat. No. 5,723,277 the disclosures of which are incorporated by reference.

In one embodiment, the blocked developer according to the present invention is used in reactive association in an imaging layer with a multifunctional coupler ("MFC"), by which is meant that the coupler has the property of forming different color dyes with the oxidized forms of distinct color developers. Preferably, the same coupler can form three different colors, preferably cyan, yellow, and magenta.

The imaging member can additionally comprise a support that can be a reflective support or a transparent support. When reflective, the support is generally white. When transparent, the support is generally clear although it can be tinted. Details of support construction are well known in the paper and photographic arts. Particular photographic supports especially useful in this invention, including subbing layers to enhance adhesion, are disclosed in *Research Disclosure*, published by Kenneth Mason Publications, Ltd., Dudley house, 12 North Street, Emsworth, Hampshire P0107DQ, England. Vol. 389, September 1996 Item 38957, XV, Supports. In another embodiment, the member can comprise a peelable support and an adhesion layer enabling a formed image to be applied to an object, as for example, to form a customized decorative item. The support can be supplied in roll or sheet form. Alternatively, the support can be a rigid member. In one embodiment, an imaging layer can be located on only one side of the support. In another embodiment, imaging layers can be located on both sides of the support to provide for double sided images, ease of use and anti-curl properties. Stabilizers, Section X, UV Stabilizers, and Section XI, Surfactants, the disclosures of which are incorporated by reference.

A multifunctional dye forming coupler can be any known coupler, or modification, variation, or derivative thereof, that possesses the requisite property of forming different color dyes with the oxidized forms of distinct color developers. Most generally, such a coupler will have Structure I:

(I)

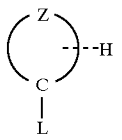

wherein:

C is a carbon atom at which coupling occurs;

L represents a hydrogen atom or a leaving group covalently bound to C and which is displaced on coupling;

H is an acidic hydrogen atom serving to direct coupling to C and which is covalently bound to C directly or by conjugation; and Z represents the remainder of the atoms of the coupler, in cyclic or acyclic form which together provide sufficient electron withdrawal to render H acidic and together provide sufficient ballast function to render the dye formed from the coupler immobile.

The coupler according to Structure I can be monomeric or polymeric in nature. Some couplers useful in the practice of this invention are described in *Research Disclosure*, Item 38957, Section X, Dye Image Formers and Modifiers; in *Research Disclosure*, Item 37038 (1995); in Katz and Fogel, *Photographic Analysis*, Morgan & Morgan, Hastings-on-Hudson, New York (1971), in the Appendix; in Lau et al, U.S. Pat. No. 5,670,302; and in European Patent Application EP 0,762,201 A1, the disclosures of which are all incorporated by reference.

In a preferred embodiment, the coupler is a pyrazole, pyrazolone, pyrazolotriazole, pyrazolotetrazole, 2-acylamino-1-naphthol or cyanoacetate coupler. Examples of such couplers are illustrated in the references cited above. Additional specific examples of these useful couplers are shown as structures M-1 through M-17 of pages 82–83, and as "Coupler 3" of page 98 right column, "Coupler 4", "Coupler 5", "Coupler 8" and "Coupler 9" of page 99, right column, "Coupler 3" of page 100, right column, and "Coupler 4" and "Coupler 5" of page 101, left column in *Research Disclosure*, Item 37038 (1995).

Some examples of preferred multifunctional dye forming couplers include, but are not limited to, the following couplers:

A-1

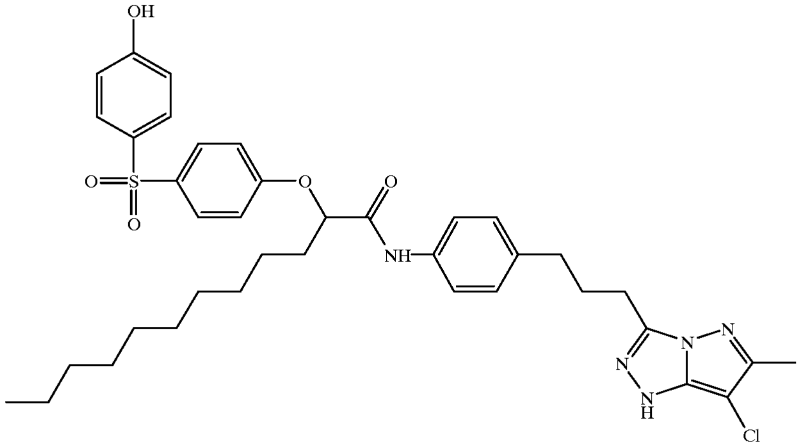

A-2

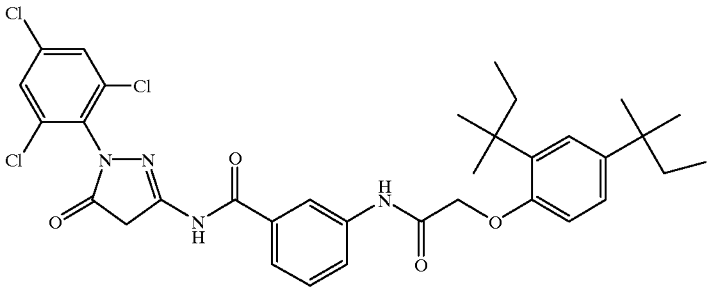

-continued
A-3
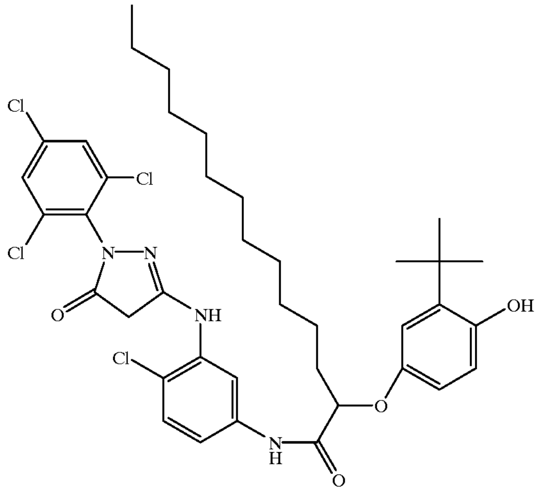
A-4
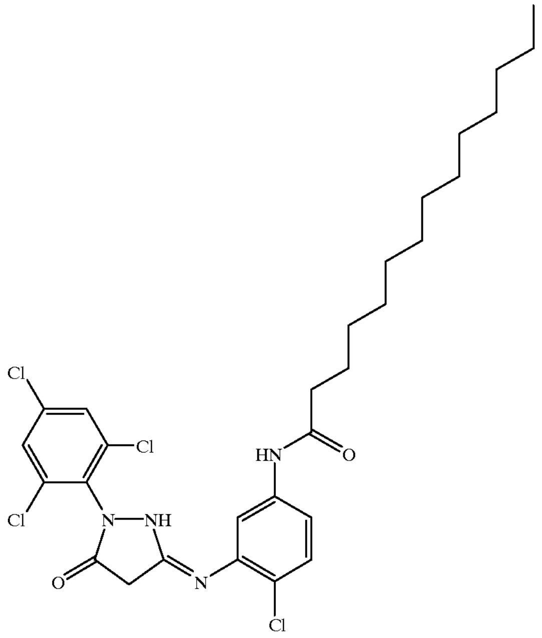

-continued
A-5
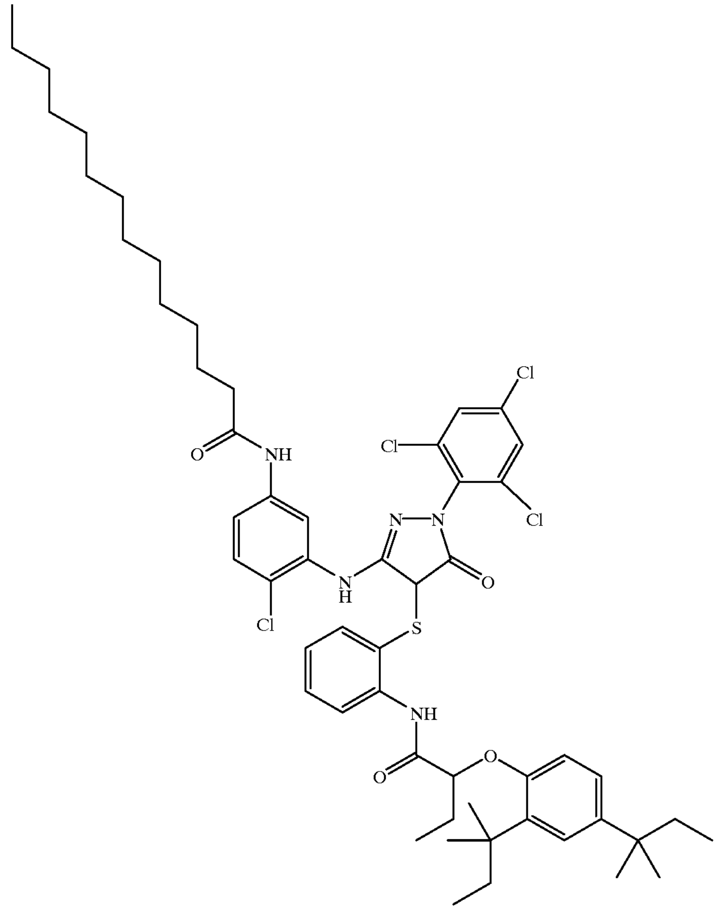
A-6
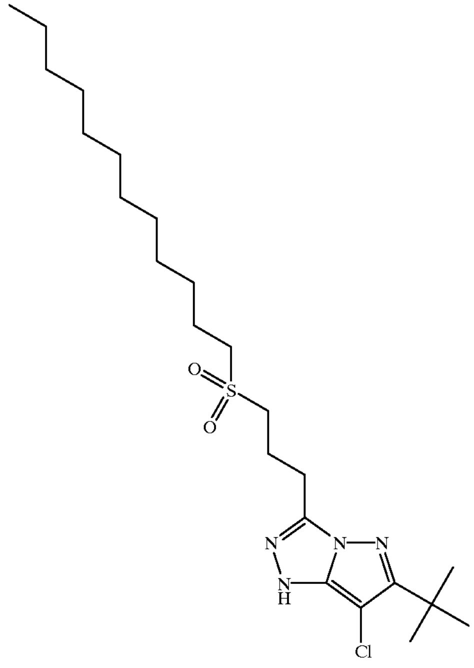

-continued
A-7
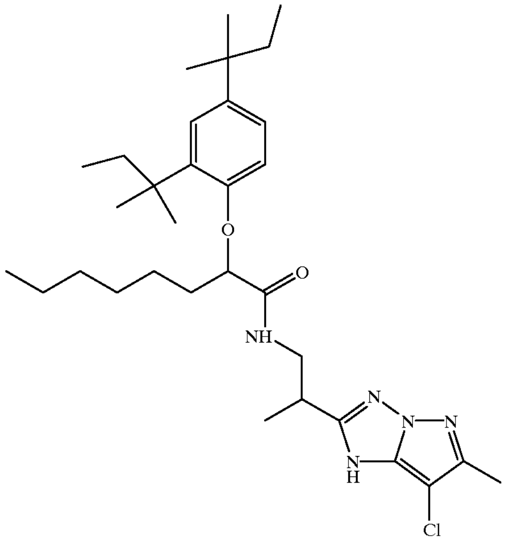
A-8
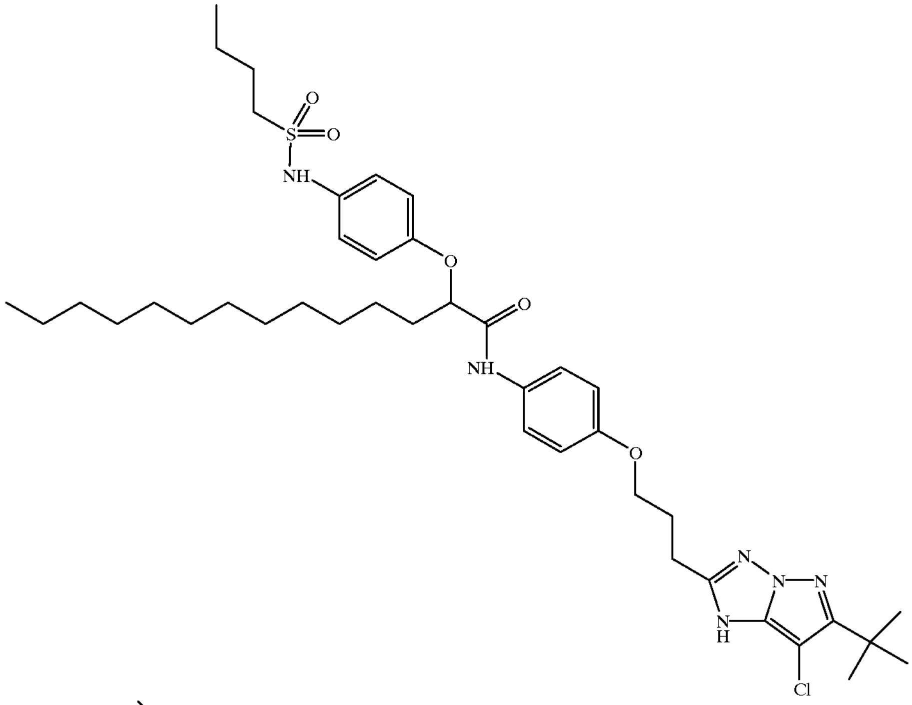
A-9
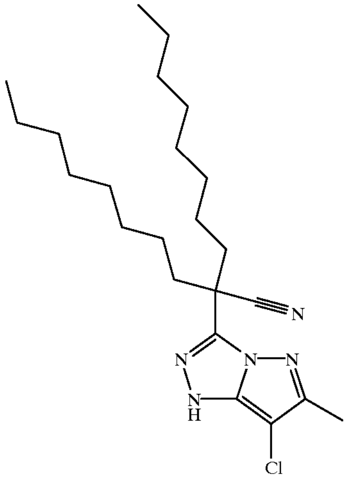

-continued
A-10
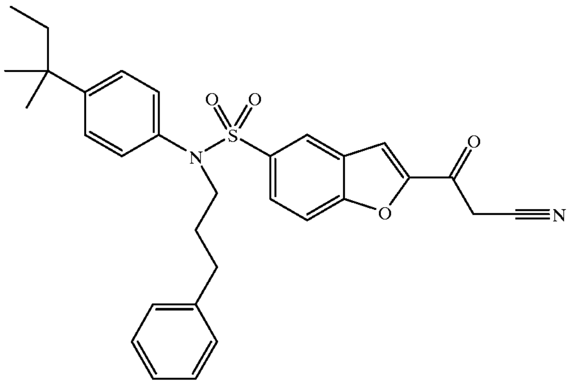
A-11
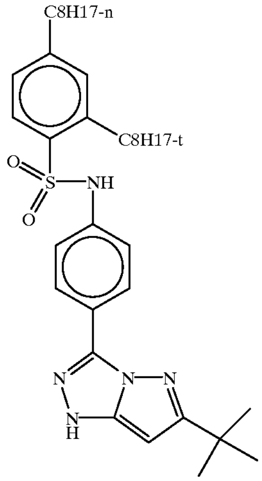
A-12
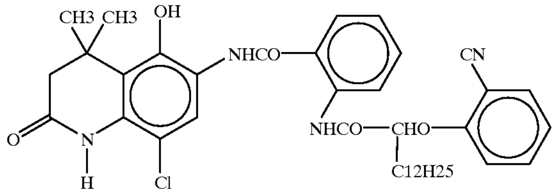
A-13
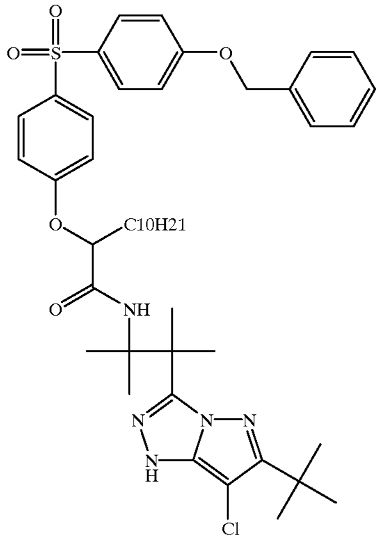

-continued

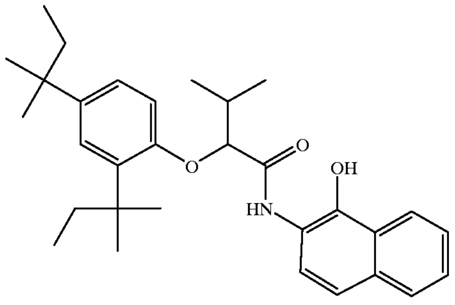

A-14

Multifunctional dye-forming couplers useful in the invention can be incorporated in the imaging member in any manner known in the art. These methods include, but are not limited to, incorporation as oil-in-water emulsions, known colloquially in the photographic arts as "dispersions", as reverse phase emulsion, as solid particle dispersions, as multiphase dispersions, as molecular dispersions or "Fisher" dispersions, or as polymer loaded dispersions or loaded latex dispersions. When the multifunctional dye forming couplers are polymeric in nature, they can additionally be incorporated merely by physically diluting the polymeric coupler with vehicle. While the multifunctional dye forming coupler can be employed in the member at any concentration that enables the desired formation of a multicolor image, it is preferred that the multifunctional dye forming coupler be applied to the member at between about 50 and 3000 mg/$m^2$. It is more preferred that the multifunctional dye forming coupler be applied to the member at between about 200 and 800 mg/$m^2$.

The imaging member can further comprise an incorporated solvent. In one embodiment, the multifunctional dye forming coupler is provided as an emulsion in such a solvent. In this embodiment, any of the high boiling organic solvents known in the photographic arts as "coupler solvents" can be employed. In this situation, the solvent acts as a manufacturing aid. Alternatively, the solvent can be incorporated separately. In both situations, the solvent can further function as a coupler stabilizer, a dye stabilizer, a reactivity enhancer or moderator, or as a hue shifting agent, all as known in the photographic arts. Additionally, auxiliary solvents can be employed to aid dissolution of the multifunctional dye forming coupler in the coupler solvent. Particulars of coupler solvents and their use are described in the aforesaid mentioned references and in Research Disclosure, Item 37038 (1995), Section IX, Solvents, and Section XI, Surfactants, incorporated herein by reference. Specific examples of some coupler solvents include, but are not limited to, tritoluyl phosphate, dibutyl phthalate, N,N-diethyldodecanamide, N,N-dibutyldodecanamide, tris(2-ethylhexyl)phosphate, acetyl tributyl citrate, 2,4-di-tert-pentylphenol, 2-(2-butoxyethoxy)ethyl acetate and 1,4-cyclohexyldimethylene bis(2-ethylhexanoate). The choice of coupler solvent and vehicle can influence the hue of dyes formed, as disclosed by Merkel et al at U.S. Pat. Nos. 4,808,502 and 4,973,535. Generally, it is found that materials with a hydrogen-bond-donating ability can shift dyes bathochromically, while materials with a hydrogen-bond-accepting ability can shift dyes hypsochromically. Additionally, use of materials with low polarizability can of itself promote hypsochromic dye hue shifts as well as promote dye aggregation. It is recognized that coupler ballasts often enable dyes and dye-coupler mixtures to function as self-solvents with a concomitant shift in hue. The polarizability, and the hydrogen-bond-donating and accepting ability of various materials are described by Kamlet et al in *J Org. Chem,* 48, 2877–87 (1983), the disclosures of which are incorporated by reference.

As indicated above, the blocked developing agent of the present invention may be in only one color unit layer in an imaging element.

Copending Commonly assigned U.S. Ser. No. 60/211,299 (docket 81248), hereby incorporated by reference discloses a light-sensitive silver-halide color photographic element having a common chromogenic coupler and a distinct developer associated with each color forming layer unit, one of which developer may be as disclosed herein. This application discloses a way of forming multiple colors from a common coupler. In a first embodiment, the light sensitive silver halide color photographic element has a red-light-sensitive silver-halide layer unit and a first blocked coupling developer, a green-light-sensitive silver-halide layer unit and a second blocked coupling developer, and a blue-light-sensitive silver-halide layer unit having a third blocked coupling developer, wherein each layer unit has the same chromogenic coupler.

Copending Commonly assigned U.S. Ser. No. 60/211,299 (docket 81248), hereby incorporated by reference discloses discloses a light sensitive color photographic imaging element comprising at least two different chromogenic couplers including, in reactive association, a multifunctional coupler and a developer precursor liberating a developing agent enabling cyan color from the multifunctional coupler on development, wherein the multifunctional coupler has the property that it is capable of forming at least one other distinctly colored dye with an oxidized form of the conventional developer 4-(N-ethyl-N-2-hydroxyethyl)-2-methylphenylenediamine. In one embodiment, the multifunctional coupler has the property that it is capable of forming a distinctly colored magenta dye with an oxidized form of the conventional developer 4-(N-ethyl-N-2-hydroxyethyl)-2-methylphenylenediamine. The latter developer (also known as "CD2"), which developer is widely used, is used herein as a standard means for the purpose of enabling a convenient color comparison, but other developers could have been substituted instead.

A typical color negative film construction useful in the practice of the invention is illustrated by the following element, SCN-1:

| Element SCN-1 | |
|---|---|
| SOC | Surface Overcoat |
| BU | Blue Recording Layer Unit |
| IL1 | First Interlayer |
| GU | Green Recording Layer Unit |
| IL2 | Second Interlayer |
| RU | Red Recording Layer Unit |
| AHU | Antihalation Layer Unit |
| S | Support |
| SOC | Surface Overcoat |

Details of support construction are well understood in the art. Examples of useful supports are poly(vinylacetal) film, polystyrene film, poly(ethyleneterephthalate) film, poly (ethylene naphthalate) film, polycarbonate film, and related films and resinous materials, as well as paper, cloth, glass, metal, and other supports that withstand the anticipated processing conditions. The element can contain additional layers, such as filter layers, interlayers, overcoat layers, subbing layers, antihalation layers and the like. Transparent and reflective support constructions, including subbing layers to enhance adhesion, are disclosed in Section XV of *Research Disclosure*, September 1996, Number 389, Item 38957 (hereafter referred to as ("*Research Disclosure I*").

The photographic elements of the invention may also usefully include a magnetic recording material as described in *Research Disclosure*, Item 34390, November 1992, or a transparent magnetic recording layer such as a layer containing magnetic particles on the underside of a transparent support as in U.S. Pat. No. 4,279,945, and U.S. Pat. No. 4,302,523.

Each of blue, green and red recording layer units BU, GU and RU are formed of one or more hydrophilic colloid layers and contain at least one radiation-sensitive silver halide emulsion, including the developing agent and, in certain embodiments, the common dye image-forming coupler. It is preferred that the green, and red recording units are subdivided into at least two recording layer sub-units to provide increased recording latitude and reduced image granularity. In the simplest contemplated construction each of the layer units or layer sub-units consists of a single hydrophilic colloid layer containing emulsion and coupler. When coupler present in a layer unit or layer sub-unit is coated in a hydrophilic colloid layer other than an emulsion containing layer, the coupler containing hydrophilic colloid layer is positioned to receive oxidized color developing agent from the emulsion during development. In this case, the coupler containing layer is usually the next adjacent hydrophilic colloid layer to the emulsion containing layer.

In order to ensure excellent image sharpness, and to facilitate manufacture and use in cameras, all of the sensitized layers are preferably positioned on a common face of the support. When in spool form, the element will be spooled such that when unspooled in a camera, exposing light strikes all of the sensitized layers before striking the face of the support carrying these layers. Further, to ensure excellent sharpness of images exposed onto the element, the total thickness of the layer units above the support should be controlled. Generally, the total thickness of the sensitized layers, interlayers and protective layers on the exposure face of the support are less than 35 $\mu$m. In another embodiment, sensitized layers disposed on two sides of a support, as in a duplitized film, can be employed.

In a preferred embodiment of this invention, the processed photographic film contains only limited amounts of color masking couplers, incorporated permanent Dmin adjusting dyes and incorporated permanent antihalation dyes. Generally, such films contain color masking couplers in total amounts up to about 0.6 mmol/$m^2$, preferably in amounts up to about 0.2 mmol/$m^2$, more preferably in amounts up to about 0.05 mmol/$m^2$, and most preferably in amounts up to about 0.01 mmol/$m^2$.

The incorporated permanent Dmin adjusting dyes are generally present in total amounts up to about 0.2 mmol/$m^2$, preferably in amounts up to about 0.1 mmol/$m^2$, more preferably in amounts up to about 0.02 mmol/$m^2$, and most preferably in amounts up to about 0.005 mmol/$M^2$.

The incorporated permanent antihalation density is up to about 0.6 in blue, green or red density, more preferably up to about 0.3 in blue, green or red density, even more preferably up to about 0.1 in blue, green or red density and most preferably up to about 0.05 in blue, green or red Status M density.

Limiting the amount of color masking couplers, permanent antihalation density and incorporated permanent Dmin adjusting dyes serves to reduce the optical density of the films, after processing, in the 350 to 750 nm range, and thus improves the subsequent scanning and digitization of the imagewise exposed and processed films.

Overall, the limited Dmin and tone scale density enabled by controlling the quantity of incorporated color masking couplers, incorporated permanent Dmin adjusting dyes and antihalation and support optical density can serve to both limit scanning noise (which increases at high optical densities), and to improve the overall signal-to-noise characteristics of the film to be scanned. Relying on the digital correction step to provide color correction obviates the need for color masking couplers in the films.

Any convenient selection from among conventional radiation-sensitive silver halide emulsions can be incorporated within the layer units and used to provide the spectral absorptances of the invention. Most commonly high bromide emulsions containing a minor amount of iodide are employed. To realize higher rates of processing, high chloride emulsions can be employed. Radiation-sensitive silver chloride, silver bromide, silver iodobromide, silver iodochloride, silver chlorobromide, silver bromochloride, silver iodochlorobromide and silver iodobromochloride grains are all contemplated. The grains can be either regular or irregular (e.g., tabular). Tabular grain emulsions, those in which tabular grains account for at least 50 (preferably at least 70 and optimally at least 90) percent of total grain projected area are particularly advantageous for increasing speed in relation to granularity. To be considered tabular a grain requires two major parallel faces with a ratio of its equivalent circular diameter (ECD) to its thickness of at least 2. Specifically preferred tabular grain emulsions are those having a tabular grain average aspect ratio of at least 5 and, optimally, greater than 8. Preferred mean tabular grain thicknesses are less than 0.3 $\mu$m (most preferably less than 0.2 $\mu$m). Ultrathin tabular grain emulsions, those with mean tabular grain thicknesses of less than 0.07 $\mu$m, are specifically contemplated. However, in a preferred embodiment, a preponderance low reflectivity grains are preferred. By preponderance is meant that greater than 50% of the grain projected area is provided by low reflectivity silver halide grains. It is even more preferred that greater than 70% of the grain projected area be provided by low reflectivity silver halide grains. Low reflective silver halide grains are those having an average grain having a grain thickness >0.06, preferably >0.08, and more preferable >0.10 microns. The grains preferably form surface latent images so that they produce negative images when processed in a surface developer in color negative film forms of the invention.

Illustrations of conventional radiation-sensitive silver halide emulsions are provided by *Research Disclosure* I, cited above, I. Emulsion grains and their preparation. Chemical sensitization of the emulsions, which can take any conventional form, is illustrated in section IV. Chemical sensitization. Compounds useful as chemical sensitizers, include, for example, active gelatin, sulfur, selenium, tellurium, gold, platinum, palladium, iridium, osmium, rhenium, phosphorous, or combinations thereof. Chemical sensitization is generally carried out at pAg levels of from 5 to 10, pH levels of from 4 to 8, and temperatures of from 30 to 80° C. Spectral sensitization and sensitizing dyes, which can take any conventional form, are illustrated by section V. Spectral sensitization and desensitization. The dye may be added to an emulsion of the silver halide grains and a hydrophilic colloid at any time prior to (e.g., during or after chemical sensitization) or simultaneous with the coating of the emulsion on a photographic element. The dyes may, for example, be added as a solution in water or an alcohol or as a dispersion of solid particles. The emulsion layers also typically include one or more antifoggants or stabilizers, which can take any conventional form, as illustrated by section VII. Antifoggants and stabilizers.

The silver halide grains to be used in the invention may be prepared according to methods known in the art, such as those described in Research Disclosure I, cited above, and James, The Theory of the Photographic Process. These include methods such as ammoniacal emulsion making, neutral or acidic emulsion making, and others known in the art. These methods generally involve mixing a water soluble silver salt with a water soluble halide salt in the presence of a protective colloid, and controlling the temperature, pAg, pH values, etc, at suitable values during formation of the silver halide by precipitation.

In the course of grain precipitation, one or more dopants (grain occlusions other than silver and halide) can be introduced to modify grain properties. For example, any of the various conventional dopants disclosed in *Research Disclosure* I, Section I. Emulsion grains and their preparation, sub-section G. Grain modifying conditions and adjustments, paragraphs (3), (4) and (5), can be present in the emulsions of the invention. In addition it is specifically contemplated to dope the grains with transition metal hexacoordination complexes containing one or more organic ligands, as taught by Olm, et al., U.S. Pat. No. 5,360,712, the disclosure of which is here incorporated by reference.

It is specifically contemplated to incorporate in the face centered cubic crystal lattice of the grains a dopant capable of increasing imaging speed by forming a shallow electron trap (hereinafter also referred to as a SET) as discussed in *Research Disclosure* Item 36736 published November 1994, here incorporated by reference.

The photographic elements of the present invention, as is typical, provide the silver halide in the form of an emulsion. Photographic emulsions generally include a vehicle for coating the emulsion as a layer of a photographic element. Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), deionized gelatin, gelatin derivatives (e.g., acetylated gelatin, phthalated gelatin, and the like), and others as described in *Research Disclosure*, I. Also useful as vehicles or vehicle extenders are hydrophilic water-permeable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers. The vehicle can be present in the emulsion in any amount useful in photographic emulsions. The emulsion can also include any of the addenda known to be useful in photographic emulsions.

While any useful quantity of light sensitive silver, as silver halide, can be employed in the elements useful in this invention, it is preferred that the total quantity be not more than 4.5 $g/m^2$ of silver, preferably less. Silver quantities of less than 4.0 $g/m^2$ are preferred, and silver quantities of less than 3.5 $g/m^2$ are even more preferred. The lower quantities of silver improve the optics of the elements, thus enabling the production of sharper pictures using the elements. These lower quantities of silver are additionally important in that they enable rapid development and desilvering of the elements. Conversely, a silver coating coverage of at least 1.0 g of coated silver per $m^2$ of support surface area in the element is necessary to realize an exposure latitude of at least 2.7 log E while maintaining an adequately low graininess position for pictures intended to be enlarged. Silver coverages in excess of 1.5 $g/m^2$ are preferred while silver coverages in excess of 2.5 $g/m^2$ are more preferred.

It is common practice to coat one, two or three separate emulsion layers within a single dye image-forming layer unit. When two or more emulsion layers are coated in a single layer unit, they are typically chosen to differ in sensitivity. When a more sensitive emulsion is coated over a less sensitive emulsion, a higher speed is realized than when the two emulsions are blended. When a less sensitive emulsion is coated over a more sensitive emulsion, a higher contrast is realized than when the two emulsions are blended. It is preferred that the most sensitive emulsion be located nearest the source of exposing radiation and the slowest emulsion be located nearest the support.

One or more of the layer units of the invention is preferably subdivided into at least two, and more preferably three or more sub-unit layers. It is preferred that all light sensitive silver halide emulsions in the color recording unit have spectral sensitivity in the same region of the visible spectrum. In this embodiment, while all silver halide emulsions incorporated in the unit have spectral absorptance according to invention, it is expected that there are minor differences in spectral absorptance properties between them. In still more preferred embodiments, the sensitizations of the slower silver halide emulsions are specifically tailored to account for the light shielding effects of the faster silver halide emulsions of the layer unit that reside above them, in order to provide an imagewise uniform spectral response by the photographic recording material as exposure varies with low to high light levels. Thus higher proportions of peak light absorbing spectral sensitizing dyes may be desirable in the slower emulsions of the subdivided layer unit to account for on-peak shielding and broadening of the underlying layer spectral sensitivity.

The interlayers IL1 and IL2 are hydrophilic colloid layers having as their primary function color contamination reduction—i.e., prevention of oxidized developing agent from migrating to an adjacent recording layer unit before reacting with dye-forming coupler. The interlayers are in part effective simply by increasing the diffusion path length that oxidized developing agent must travel. To increase the effectiveness of the interlayers to intercept oxidized developing agent, it is conventional practice to incorporate oxidized developing agent. Antistain agents (oxidized developing agent scavengers) can be selected from among those disclosed by *Research Disclosure* I, X. Dye image formers and modifiers, D. Hue modifiers/stabilization, paragraph (2). When one or more silver halide emulsions in GU and RU are high bromide emulsions and, hence have significant native sensitivity to blue light, it is preferred to incorporate a yellow filter, such as Carey Lea silver or a yellow processing solution decolorizable dye, in IL1. Suitable yellow filter dyes can be selected from among those illustrated by Research Disclosure I, Section VIII. Absorbing and scattering materials, B. Absorbing materials. In elements of the instant invention, magenta colored filter materials are absent from IL2 and RU.

The antihalation layer unit AHU typically contains a processing solution removable or decolorizable light absorbing material, such as one or a combination of pigments and dyes. Suitable materials can be selected from among those disclosed in *Research Disclosure* I, Section VIII. Absorbing materials. A common alternative location for AHU is between the support S and the recording layer unit coated nearest the support.

The surface overcoats SOC are hydrophilic colloid layers that are provided for physical protection of the color negative elements during handling and processing. Each SOC also provides a convenient location for incorporation of addenda that are most effective at or near the surface of the color negative element. In some instances the surface overcoat is divided into a surface layer and an interlayer, the latter functioning as spacer between the addenda in the surface layer and the adjacent recording layer unit. In another common variant form, addenda are distributed between the surface layer and the interlayer, with the latter containing addenda that are compatible with the adjacent recording layer unit. Most typically the SOC contains addenda, such as coating aids, plasticizers and lubricants, antistats and matting agents, such as illustrated by *Research Disclosure* I, Section IX. Coating physical property modifying addenda. The SOC overlying the emulsion layers additionally preferably contains an ultraviolet absorber, such as illustrated by *Research Disclosure* I, Section VI. UV dyes/optical brighteners/luminescent dyes, paragraph (1).

Instead of the layer unit sequence of element SCN-1, alternative layer units sequences can be employed and are particularly attractive for some emulsion choices. Using high chloride emulsions and/or thin (<0.2 $\mu$m mean grain thickness) tabular grain emulsions all possible interchanges of the positions of BU, GU and RU can be undertaken without risk of blue light contamination of the minus blue records, since these emulsions exhibit negligible native sensitivity in the visible spectrum. For the same reason, it is unnecessary to incorporate blue light absorbers in the interlayers.

When the emulsion layers within a dye image-forming layer unit differ in speed, it is conventional practice to limit the incorporation of dye image-forming coupler in the layer of highest speed to less than a stoichiometric amount, based on silver. The function of the highest speed emulsion layer is to create the portion of the characteristic curve just above the minimum density—i.e., in an exposure region that is below the threshold sensitivity of the remaining emulsion layer or layers in the layer unit. In this way, adding the increased granularity of the highest sensitivity speed emulsion layer to the dye image record produced is minimized without sacrificing imaging speed.

In the foregoing discussion the blue, green and red recording layer units are described as containing developing agents for producing yellow, magenta and cyan dyes, respectively, as is conventional practice in color negative elements used for printing. The invention can be suitably applied to conventional color negative construction as illustrated. Color reversal film construction would take a similar form, with the exception that colored masking couplers would be completely absent; in typical forms, development inhibitor releasing couplers would also be absent. In preferred embodiments, the color negative elements are intended exclusively for scanning to produce three separate electronic color records. Thus the actual hue of the image dye produced is of no importance. What is essential is merely that the dye image produced in each of the layer units be differentiable from that produced by each of the remaining layer units. To provide this capability of differentiation it is contemplated that each of the layer units contain one or more dye image-forming couplers chosen to produce image dye having an absorption half-peak bandwidth lying in a different spectral region. It is immaterial whether the blue, green or red recording layer unit forms a yellow, magenta or cyan dye having an absorption half peak bandwidth in the blue, green or red region of the spectrum, as is conventional in a color negative element intended for use in printing, so long as the absorption half-peak bandwidths of the image dye in the layer units extend over substantially non-coextensive wavelength ranges. The term "substantially non-coextensive wavelength ranges" means that each image dye exhibits an absorption half-peak band width that extends over at least a 25 nm (preferably 50 nm) spectral region that is not occupied by an absorption half-peak band width of another image dye. Ideally the image dyes exhibit absorption half-peak band widths that are mutually exclusive.

When a layer unit contains two or more emulsion layers differing in speed, it is possible to lower image granularity in the image to be viewed, recreated from an electronic record, by forming in each emulsion layer of the layer unit a dye image which exhibits an absorption half-peak band width that lies in a different spectral region than the dye images of the other emulsion layers of layer unit. This technique is particularly well suited to elements in which the layer units are divided into sub-units that differ in speed. This allows multiple electronic records to be created for each layer unit, corresponding to the differing dye images formed by the emulsion layers of the same spectral sensitivity. The digital record formed by scanning the dye image formed by an emulsion layer of the highest speed is used to recreate the portion of the dye image to be viewed lying just above minimum density. At higher exposure levels second and, optionally, third electronic records can be formed by scanning spectrally differentiated dye images formed by the remaining emulsion layer or layers. These digital records contain less noise (lower granularity) and can be used in recreating the image to be viewed over exposure ranges above the threshold exposure level of the slower emulsion layers. This technique for lowering granularity is disclosed in greater detail by Sutton U.S. Pat. No. 5,314,794, the disclosure of which is here incorporated by reference.

Each layer unit of the color negative elements of the invention produces a dye image characteristic curve gamma of less than 1.5, which facilitates obtaining an exposure latitude of at least 2.7 log E. A minimum acceptable exposure latitude of a multicolor photographic element is that which allows accurately recording the most extreme whites (e.g., a bride's wedding gown) and the most extreme blacks (e.g., a bride groom's tuxedo) that are likely to arise in photographic use. An exposure latitude of 2.6 log E can just accommodate the typical bride and groom wedding scene.

An exposure latitude of at least 3.0 log E is preferred, since this allows for a comfortable margin of error in exposure level selection by a photographer. Even larger exposure latitudes are specifically preferred, since the ability to obtain accurate image reproduction with larger exposure errors is realized. Whereas in color negative elements intended for printing, the visual attractiveness of the printed scene is often lost when gamma is exceptionally low, when color negative elements are scanned to create digital dye image records, contrast can be increased by adjustment of the electronic signal information. When the elements of the invention are scanned using a reflected beam, the beam travels through the layer units twice. This effectively doubles gamma ($\Delta D \div \Delta$ log E) by doubling changes in density ($\Delta D$). Thus, gamma's as low as 1.0 or even 0.6 are contemplated and exposure latitudes of up to about 5.0 log E or higher are feasible. Gammas above 0.25 are preferred and gammas above 0.30 are more preferred. Gammas of between about 0.4 and 0.5 are especially preferred.

In a preferred embodiment the dye image is formed by the use of an incorporated developing agent, in reactive association with each color layer. More preferably, the incorporated developing agent is a blocked developing agent.

Examples of blocked developers that can be used in photographic elements of the present invention include, but are not limited to, the blocked developing agents described in U.S. Pat. No. 3,342,599, to Reeves; *Research Disclosure* (129 (1975) pp. 27–30) published by Kenneth Mason Publications, Ltd., Dudley Annex, 12a North Street, Emsworth, Hampshire P0107DQ, ENGLAND; U.S. Pat. No. 4,157,915, to Hamaoka et al.; U.S. Pat. No. 4, 060,418, to Waxman and Mourning; and in U.S. Pat. No. 5,019,492. Other examples of blocked developers that can be used in photographic elements of the present invention include, but are not limited to, the blocked developing agents described in U.S. Pat. No. 3,342,599, to Reeves; *Research Disclosure* (129 (1975) pp. 27–30) published by Kenneth Mason Publications, Ltd., Dudley Annex, 12a North Street, Emsworth, Hampshire P0107DQ, ENGLAND; U.S. Pat. No. 4,157,915, to Hamaoka et al.; U.S. Pat. No. 4,060,418, to Waxman and Mourning; and in U.S. Pat. No. 5,019,492. Particularly useful are those blocked developers described in U.S. application Ser. No. 09/476,234, filed Dec. 30, 1999, IMAGING ELEMENT CONTAINING A BLOCKED PHOTOGRAPICALLY USEFUL COMPOUND; U.S. application Ser. No. 09/475,691, filed Dec. 30, 1999, IMAGING ELEMENT CONTAINING A BLOCKED PHOTOGRAPHICALLY USEFUL COMPOUND; U.S. application Ser. No. 09/475,703, filed Dec. 30, 1999, IMAGING ELEMENT CONTAINING A BLOCKED PHOTOGRAPHICALLY USEFUL COMPOUND; U.S. application Ser. No. 09/475,690, filed Dec. 30, 1999, IMAGING ELEMENT CONTAINING A BLOCKED PHOTOGRAPHICALLY USEFUL COMPOUND; and U.S. application Ser. No. 09/476,233, filed Dec. 30, 1999, PHOTOGRAPHIC OR PHOTOTHERMOGRAPHIC ELEMENT CONTAINING A BLOCKED PHOTOGRAPHICALLY USEFUL COMPOUND. In one embodiment of the invention, the blocked developer may be respresented by the following Structure I:

$$\text{DEV—(LINK 1)}_1\text{—(TIME)}_m\text{—(LINK 2)}_n\text{—B}$$

I wherein,

DEV is a silver-halide color developing agent;

LINK 1 and LINK 2 are linking groups;

TIME is a timing group;

1 is 0 or 1;

m is 0, 1,or 2;

n is 0 or 1;

1+n is 1 or 2;

B is a blocking group or B is:

$$\text{—B'—(LINK 2)}_n\text{—(TIME)}_m\text{—(LINK 1)}_1\text{—DEV}$$

wherein B' also blocks a second developing agent DEV.

In a preferred embodiment of the invention, LINK 1 or LINK 2 are of structure II:

II

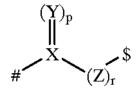

wherein

X represents carbon or sulfur;

Y represents oxygen, sulfur of N—$R_1$, where $R_1$ is substituted or unsubstituted alkyl or substituted or unsubstituted aryl;

p is 1 or 2;

Z represents carbon, oxygen or sulfur;

r is 0 or 1;

with the proviso that when X is carbon, both p and r are 1, when X is sulfur, Y is oxygen, p is 2 and r is 0;

# denotes the bond to PUG (for LINK 1) or TIME (for LINK 2):

$ denotes the bond to TIME (for LINK 1) or T(t) substituted carbon (for LINK 2).

Illustrative linking groups include, for example,

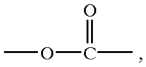 , 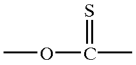 , 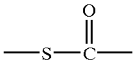 ,

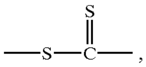 , Or 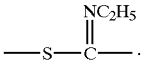 .

TIME is a timing group. Such groups are well-known in the art such as (1) groups utilizing an aromatic nucleophilic substitution reaction as disclosed in U.S. Pat. No. 5,262,291; (2) groups utilizing the cleavage reaction of a hemiacetal (U.S. Pat. No. 4,146,396, Japanese Applications 60-249148; 60-249149); (3) groups utilizing an electron transfer reaction along a conjugated system (U.S. Pat. Nos. 4,409,323; 4,421, 845; Japanese Applications 57-188035; 58-98728; 58-209736; 58-209738); and (4) groups using an intramolecular nucleophilic substitution reaction (U.S. Pat. No. 4,248,962).

Illustrative timing groups are illustrated by formulae T-1 through T-4.

T-1

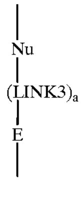

wherein:

Nu is a nucleophilic group;

E is an electrophilic group comprising one or more carbo- or hetero-aromatic rings, containing an electron deficient carbon atom;

LINK 3 is a linking group that provides 1 to 5 atoms in the direct path between the nucleopnilic site of Nu and the electron deficient carbon atom in E; and a is 0 or 1.

Such timing groups include, for example:

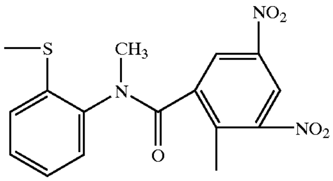

and

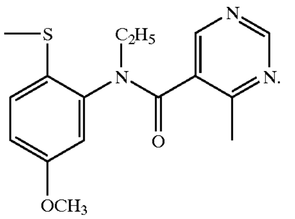

These timing groups are described more fully in U.S. Pat. No. 5,262,291, incorporated herein by reference.

T-2

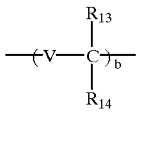

wherein

V represents an oxygen atom, a sulfur atom, or an

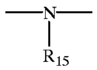

group;

$R_{13}$ and $R_{14}$ each represents a hydrogen atom or a substituent group;

$R_{15}$ represents a substituent group; and b represents 1 or 2.

Typical examples of $R_{13}$ and $R_{14}$, when they represent substituent groups, and $R_{15}$ include $R_{16}$—, $R_{17}CO$—, $R_{17}SO_2$—,

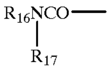

and

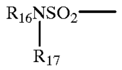

where, $R_{16}$ represents an aliphatic or aromatic hydrocarbon residue, or a heterocyclic group; and $R_{17}$ represents a hydrogen atom, an aliphatic or aromatic hydrocarbon residue, or a heterocyclic group, $R_{13}$, $R_{14}$ and $R_{15}$ each may represent a divalent group, and any two of them combine with each other to complete a ring structure. Specific examples of the group represented by formula (T-2) are illustrated below.

—$OCH_2$—,

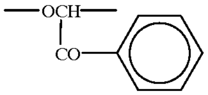

,

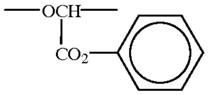

, —$SCH_2$—,

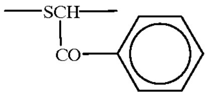

,

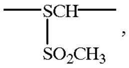

,

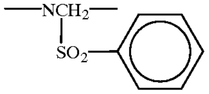

,

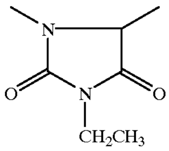

, and

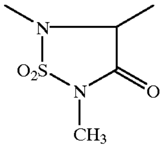

T-3

—Nu1—LINK4—E1— wherein Nu 1 represents a nucleophilic group, and an oxygen or sulfur atom can be given as an example of nucleophilic species; E1 represents an electrophilic group being a group which is subjected to nucleophilic attack by Nu 1; and LINK 4 represents a linking group which enables Nu 1 and E1 to have a steric arrangement such that an intramolecular nucleophilic substitution reaction can occur. Specific examples of the group represented by formula (T-3) are illustrated below.

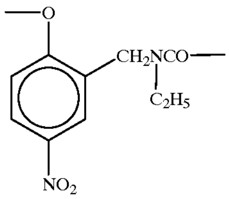

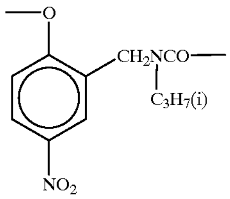

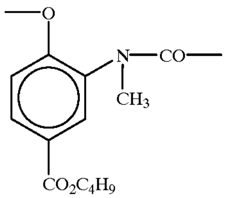

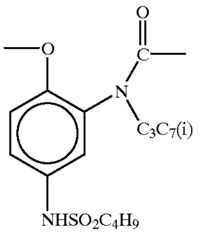

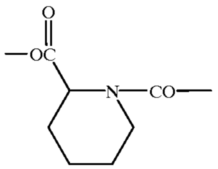

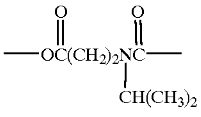

-continued

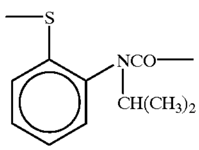

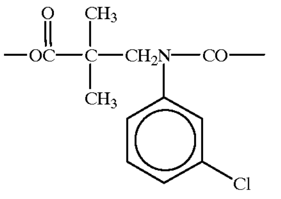

T-4

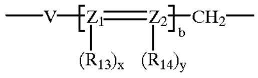

wherein V, $R_{13}$, $R_{14}$ and b all have the same meaning as in formula (T-2), respectively. In addition, $R_{13}$ and $R_{14}$ may be joined together to form a benzene ring or a heterocyclic ring, or V may be joined with $R_{13}$ or $R_{14}$ to form a benzene or heterocyclic ring. $Z_1$ and $Z_2$ each independently represents a carbon atom or a nitrogen atom, and x and y each represents 0 or 1.

Specific examples of the timing group (T-4) are illustrated below.

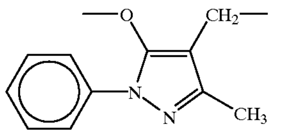

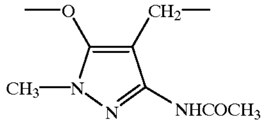

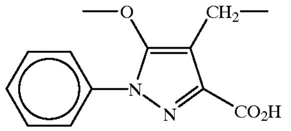

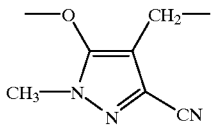

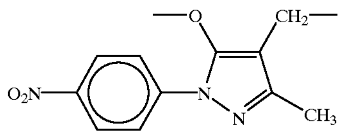

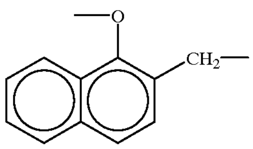

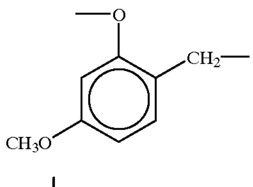

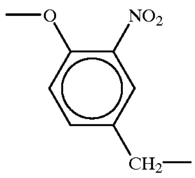

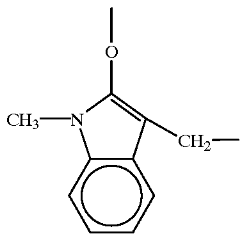

-continued

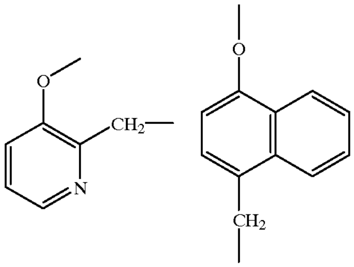

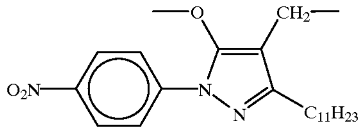

The following are merely some examples of photographically useful blocked developers that may be used according to the present invention.

D-1

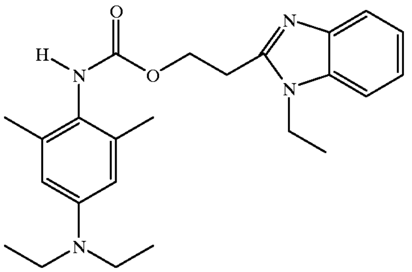

D-2

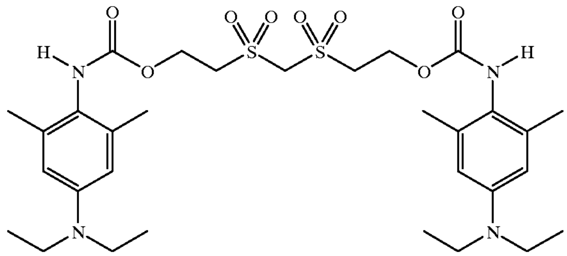

D-3

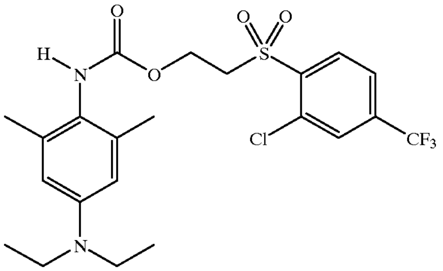

-continued

D-4

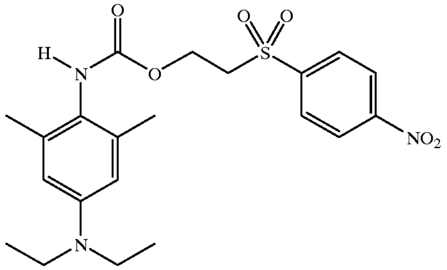

D-5

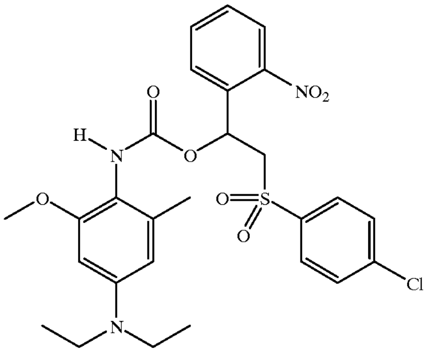

D-6

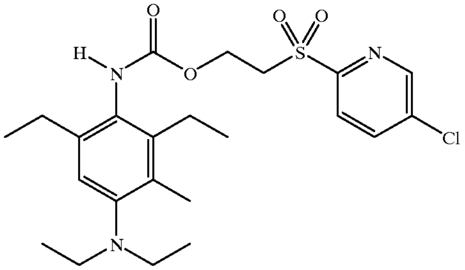

D-7

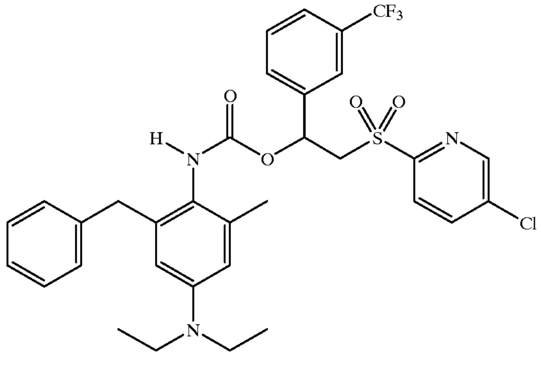

D-8

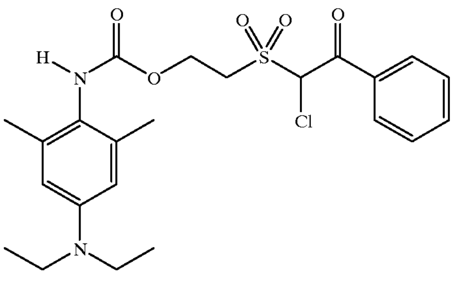

-continued

D-9

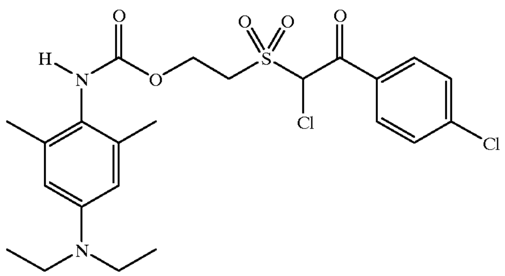

D-10

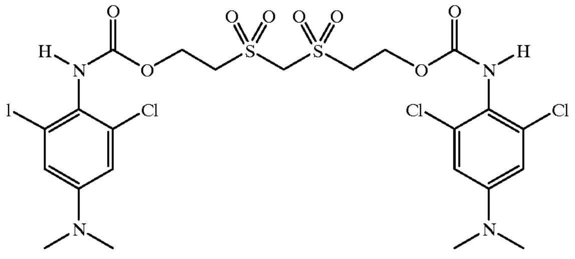

D-11

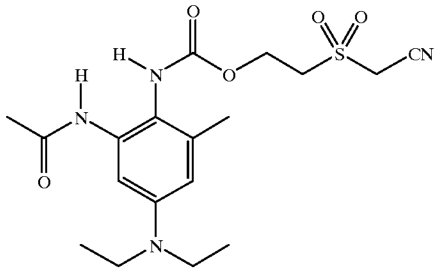

D-12

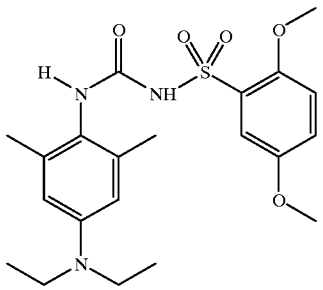

A number of modifications of color negative elements have been suggested for accommodating scanning, as illustrated by *Research Disclosure* I, Section XIV, Scan facilitating features. These systems to the extent compatible with the color negative element constructions described above are contemplated for use in the practice of this invention.

It is also contemplated that the imaging element of this invention may be used with non-conventional sensitization schemes. For example, instead of using imaging layers sensitized to the red, green, and blue regions of the spectrum, the light-sensitive material may have one white-sensitive layer to record scene luminance, and two color-sensitive layers to record scene chrominance. Following development, the resulting image can be scanned and digitally reprocessed to reconstruct the full colors of the original scene as described in U.S. Pat. No. 5,962,205. The imaging element may also comprise a pan-sensitized emulsion with accompanying color-separation exposure. In this embodiment, the developers of the invention would give rise to a colored or neutral image that, in conjunction with the separation exposure, would enable full recovery of the original scene color values. In such an element, the image may be formed by either developed silver density, a combination of one or more conventional couplers, or "black" couplers such as resorcinol couplers. The separation exposure may be made either sequentially through appropriate filters, or simultaneously through a system of spatially discreet filter elements (commonly called a "color filter array").

The imaging element of the invention may also be a black and white image-forming material comprised, for example, of a pan-sensitized silver halide emulsion and a developer of the invention. In this embodiment, the image may be formed by developed silver density following processing, or by a coupler that generates a dye which can be used to carry the neutral image tone scale.

When conventional yellow, magenta, and cyan image dyes are formed to read out the recorded scene exposures following chemical development of conventional exposed color photographic materials, the response of the red, green, and blue color recording units of the element can be accurately discerned by examining their densities. Densitometry is the measurement of transmitted light by a sample using selected colored filters to separate the imagewise response of the RGB image dye forming units into relatively independent channels. It is common to use Status M filters to gauge the response of color negative film elements intended for optical printing, and Status A filters for color reversal films intended for direct transmission viewing. In integral densitometry, the unwanted side and tail absorptions of the imperfect image dyes leads to a small amount of channel mixing, where part of the total response of, for example, a magenta channel may come from off-peak absorptions of either the yellow or cyan image dyes records, or both, in neutral characteristic curves. Such artifacts may be negligible in the measurement of a film's spectral sensitivity. By appropriate mathematical treatment of the integral density response, these unwanted off-peak density contributions can be completely corrected providing analytical densities, where the response of a given color record is independent of the spectral contributions of the other image dyes. Analytical density determination has been summarized in the *SPSE Handbook of Photographic Science and Engineering*, W. Thomas, editor, John Wiley and Sons, New York, 1973, Section 15.3, Color Densitometry, pp. 840–848.

Image noise can be reduced, where the images are obtained by scanning exposed and processed color negative film elements to obtain a manipulatable electronic record of the image pattern, followed by reconversion of the adjusted electronic record to a viewable form. Image sharpness and colorfulness can be increased by designing layer gamma ratios to be within a narrow range while avoiding or minimizing other performance deficiencies, where the color record is placed in an electronic form prior to recreating a color image to be viewed. Whereas it is impossible to separate image noise from the remainder of the image information, either in printing or by manipulating an electronic image record, it is possible by adjusting an electronic image record that exhibits low noise, as is provided by color negative film elements with low gamma ratios, to improve overall curve shape and sharpness characteristics in a manner that is impossible to achieve by known printing techniques. Thus, images can be recreated from electronic image records derived from such color negative elements that are superior to those similarly derived from conventional color negative elements constructed to serve optical printing applications. The excellent imaging characteristics of the described element are obtained when the gamma ratio for each of the red, green and blue color recording units is less than 1.2. In a more preferred embodiment, the red, green, and blue light sensitive color forming units each exhibit gamma ratios of less than 1.15. In an even more preferred embodiment, the red and blue light sensitive color forming units each exhibit gamma ratios of less than 1.10. In a most preferred embodiment, the red, green, and blue light sensitive color forming units each exhibit gamma ratios of less than 1.10. In all cases, it is preferred that the individual color unit(s) exhibit gamma ratios of less than 1.15, more preferred that they exhibit gamma ratios of less than 1.10 and even more preferred that they exhibit gamma ratios of less than 1.05. In a like vein, it is preferred that the gamma ratios be greater than 0.8, more preferred that they be greater than 0.85 and most preferred that they be greater than 0.9. The gamma ratios of the layer units need not be equal. These low values of the gamma ratio are indicative of low levels of interlayer interaction, also known as interlayer interimage effects, between the layer units and are believed to account for the improved quality of the images after scanning and electronic manipulation. The apparently deleterious image characteristics that result from chemical interactions between the layer units need not be electronically suppressed during the image manipulation activity. The interactions are often difficult if not impossible to suppress properly using known electronic image manipulation schemes.

Elements having excellent light sensitivity are best employed in the practice of this invention. The elements should have a sensitivity of at least about ISO 50, preferably have a sensitivity of at least about ISO 100, and more preferably have a sensitivity of at least about ISO 200. Elements having a sensitivity of up to ISO 3200 or even higher are specifically contemplated. The speed, or sensitivity, of a color negative photographic element is inversely related to the exposure required to enable the attainment of a specified density above fog after processing. Photographic speed for a color negative element with a gamma of about 0.65 in each color record has been specifically defined by the American National Standards Institute (ANSI) as ANSI Standard Number PH 2.27-1981 (ISO (ASA Speed)) and relates specifically the average of exposure levels required to produce a density of 0.15 above the minimum density in each of the green light sensitive and least sensitive color recording unit of a color film. This definition conforms to the International Standards Organization (ISO) film speed rating. For the purposes of this application, if the color unit gammas differ from 0.65, the ASA or ISO speed is to be calculated by linearly amplifying or deamplifying the gamma vs. log E (exposure) curve to a value of 0.65 before determining the speed in the otherwise defined manner.

The present invention also contemplates the use of photographic (including photothermographic) elements of the present invention in what are often referred to as single use cameras (or "film with lens" units). These cameras are sold with film preloaded in them and the entire camera is returned to a processor with the exposed film remaining inside the camera. The one-time-use cameras employed in this invention can be any of those known in the art. These cameras can provide specific features as known in the art such as shutter means, film winding means, film advance means, waterproof housings, single or multiple lenses, lens selection means, variable aperture, focus or focal length lenses, means for monitoring lighting conditions, means for adjusting shutter times or lens characteristics based on lighting conditions or user provided instructions, and means for camera recording use conditions directly on the film. These features include, but are not limited to: providing simplified mechanisms for manually or automatically advancing film and resetting shutters as described at Skarman, U.S. Pat. No. 4,226,517; providing apparatus for automatic exposure control as described at Matterson et al, U.S. Pat. No. 4,345,835; moisture-proofing as described at Fujimura et al, U.S. Pat. No. 4,766,451; providing internal and external film casings as described at Ohmura et al, U.S. Pat. No. 4,751,536; providing means for recording use conditions on the film as described at Taniguchi et al, U.S. Pat. No. 4,780,735; providing lens fitted cameras as described at Arai, U.S. Pat. No. 4,804,987; providing film supports with superior anti-curl properties as described at Sasaki et al, U.S. Pat. No. 4,827,298; providing a viewfinder as described at Ohmura et al, U.S. Pat. No. 4,812,863; providing a lens of defined focal length and lens speed as described at Ushiro et al, U.S. Pat. No. 4,812,866; providing multiple film containers as described at Nakayama et al, U.S. Pat. No. 4,831,398 and at Ohmura et al, U.S. Pat. No. 4,833,495; providing films with improved anti-friction characteristics as described at Shiba, U.S. Pat. No. 4,866,469; providing winding mechanisms, rotating spools, or resilient sleeves as described at Mochida, U.S. Pat. No. 4,884,087; providing a film patrone or cartridge removable in an axial direction as described by Takei et al at U.S. Pat. Nos. 4,890,130 and 5,063,400; providing an electronic flash means as described at Ohmura et al, U.S. Pat. No. 4,896,178; providing an externally operable member for effecting exposure as described at Mochida et al, U.S. Pat. No. 4,954,857; providing film support with modified sprocket holes and means for advancing said film as described at Murakami, U.S. Pat. No. 5,049,908; providing internal mirrors as described at Hara, U.S. Pat. No. 5,084,719; and providing silver halide emulsions suitable for use on tightly wound spools as described at Yagi et al, European Patent Application 0,466,417 A.

While the film may be mounted in the one-time-use camera in any manner known in the art, it is especially preferred to mount the film in the one-time-use camera such that it is taken up on exposure by a thrust cartridge. Thrust cartridges are disclosed by Kataoka et al U.S. Pat. No. 5,226,613; by Zander U.S. Pat. No. 5,200,777; by Dowling et al U.S. Pat. No. 5,031,852; and by Robertson et al U.S. Pat. No. 4,834,306. Narrow bodied one-time-use cameras suitable for employing thrust cartridges in this way are described by Tobioka et al U.S. Pat. No. 5,692,221.

Cameras may contain a built-in processing capability, for example a heating element. Designs for such cameras including their use in an image capture and display system are disclosed in Stoebe, et al., U.S. patent application Ser. No. 09/388,573 filed Sep. 1, 1999, incorporated herein by reference. The use of a one-time use camera as disclosed in said application is particularly preferred in the practice of this invention.

Photographic elements of the present invention are preferably imagewise exposed using any of the known techniques, including those described in *Research Disclosure* I, Section XVI. This typically involves exposure to light in the visible region of the spectrum, and typically such exposure is of a live image through a lens, although exposure can also be exposure to a stored image (such as a computer stored image) by means of light emitting devices (such as light emitting diodes, CRT and the like). The photothermographic elements are also exposed by means of various forms of energy, including ultraviolet and infrared regions of the electromagnetic spectrum as well as electron beam and beta radiation, gamma ray, x-ray, alpha particle, neutron radiation and other forms of corpuscular wave-like radiant energy in either non-coherent (random phase) or coherent (in phase) forms produced by lasers. Exposures are monochromatic, orthochromatic, or panchromatic depending upon the spectral sensitization of the photographic silver halide.

The elements as discussed above may serve as origination material for some or all of the following process steps: image scanning to produce an electronic rendition of the capture image, and subsequent digital processing of that rendition to manipulate, store, transmit, output, or display electronically that image.

As mentioned above, the photographic elements of the present invention can be photothermographic elements, for example of the type described in *Research Disclosure*, June 1978, Item No. 17029 (hereafter "Research Disclosure I") are included by reference, and as also described in more recent patents in the photothermographic field. The photothermographic elements may be of the type A or type B disclosed in Research Disclosure I. Type A elements contain in reactive association a photosensitive silver halide, a reducing agent or developer, an activator, and a coating vehicle or binder. In these systems development occurs by reduction of silver ions in the photosensitive silver halide to metallic silver. Type B systems can contain all of the elements of a type A system in addition to a salt or complex of an organic compound with silver ion. In these systems, this organic complex is reduced during development to yield silver metal. The organic silver salt will be referred to as the silver donor. References describing such imaging elements include, for example, U.S. Pat. Nos. 3,457,075; 4,459,350; 4,264,725 and 4,741,992.

A photothermographic element comprises a photosensitive component that consists essentially of photographic silver halide. In the type B photothermographic material it is believed that the latent image silver from the silver halide acts as a catalyst for the described image-forming combination upon processing. In these systems, a preferred concentration of photographic silver halide is within the range of 0.01 to 100 moles of photographic silver halide per mole of silver donor in the photothermographic material.

The Type B photothermographic element comprises an oxidation-reduction image forming combination that contains an organic silver salt oxidizing agent. The organic silver salt is a silver salt which is comparatively stable to light, but aids in the formation of a silver image when heated to 80° C. or higher in the presence of an exposed photocatalyst (i.e., the photosensitive silver halide) and a reducing agent.

Suitable organic silver salts include silver salts of organic compounds having a carboxyl group. Preferred examples thereof include a silver salt of an aliphatic carboxylic acid and a silver salt of an aromatic carboxylic acid. Preferred examples of the silver salts of aliphatic carboxylic acids include silver behenate, silver stearate, silver oleate, silver laureate, silver caprate, silver myristate, silver palmitate, silver maleate, silver fumarate, silver tartarate, silver furoate, silver linoleate, silver butyrate and silver camphorate, mixtures thereof, etc. Silver salts which are substitutable with a halogen atom or a hydroxyl group can also be effectively used. Preferred examples of the silver salts of aromatic carboxylic acid and other carboxyl group-containing compounds include silver benzoate, a silver-substituted benzoate such as silver 3,5-dihydroxybenzoate, silver o-methylbenzoate, silver m-methylbenzoate, silver p-methylbenzoate, silver 2,4-dichlorobenzoate, silver acetamidobenzoate, silver p-phenylbenzoate, etc., silver gallate, silver tannate, silver phthalate, silver terephthalate, silver salicylate, silver phenylacetate, silver pyromellilate, a silver salt of 3-carboxymethyl-4-methyl-4-thiazoline-2-thione or the like as described in U.S. Pat. No. 3,785,830, and silver salt of an aliphatic carboxylic acid containing a thioether group as described in U.S. Pat. No. 3,330,663.

Furthermore, a silver salt of a compound containing an imino group can be used. Preferred examples of these compounds include a silver salt of benzotriazole and a derivative thereof as described in Japanese patent publications 30270/69 and 18146/70, for example a silver salt of benzotriazole or methylbenzotriazole, etc., a silver salt of a halogen substituted benzotriazole, such as a silver salt of 5-chlorobenzotriazole, etc., a silver salt of 1,2,4-triazole, a silver salt of 3-amino-5-mercaptobenzyl-1,2,4-triazole, of lH-tetrazole as described in U.S. Pat. No. 4,220,709, a silver salt of imidazole and an imidazole derivative, and the like.

The photosensitive silver halide grains and the organic silver salt are coated so that they are in catalytic proximity during development. They can be coated in contiguous layers, but are preferably mixed prior to coating. Conventional mixing techniques are illustrated by *Research Disclosure*, Item 17029, cited above, as well as U.S. Pat. No. 3,700,458 and published Japanese patent applications Nos. 32928/75, 13224/74, 17216/75 and 42729/76.

The photothermographic element can comprise a thermal solvent. Examples of useful thermal solvents. Examples of thermal solvents, for example, salicylanilide, phthalimide, N-hydroxyphthalimide, N-potassium-phthalimide, succinimide, N-hydroxy-1,8-naphthalimide, phthalazine, 1-(2H)-phthalazinone, 2-acetylphthalazinone, benzanilide, and benzenesulfonamide. Prior-art thermal solvents are disclosed, for example, in U.S. Pat. No. 6,013,420 to Windender. Examples of toning agents and toning agent combinations are described in, for example, *Research Disclosure*, June 1978, Item No. 17029 and U.S. Pat. No. 4,123,282.

Photothermographic elements as described can contain addenda that are known to aid in formation of a useful image. The photothermographic element can contain development modifiers that function as speed increasing compounds, sensitizing dyes, hardeners, antistatic agents, plasticizers and lubricants, coating aids, brighteners, absorbing and filter dyes, such as described in Research Disclosure, December 1978, Item No. 17643 and *Research Disclosure*, June 1978, Item No. 17029.

After imagewise exposure of a photothermographic element, the resulting latent image can be developed in a variety of ways. The simplest is by overall heating the element to thermal processing temperature. This overall heating merely involves heating the photothermographic element to a temperature within the range of about 90° C. to about 180° C. until a developed image is formed, such as within about 0.5 to about 60 seconds. By increasing or decreasing the thermal processing temperature a shorter or longer time of processing is useful. A preferred thermal processing temperature is within the range of about 100° C. to about 160° C. Heating means known in the photothermographic arts are useful for providing the desired processing temperature for the exposed photothermographic element. The heating means is, for example, a simple hot plate, iron, roller, heated drum, microwave heating means, heated air, vapor or the like.

It is contemplated that the design of the processor for the photothermographic element be linked to the design of the cassette or cartridge used for storage and use of the element. Further, data stored on the film or cartridge may be used to modify processing conditions or scanning of the element. Methods for accomplishing these steps in the imaging system are disclosed by Stoebe, et al., U.S. Pat. No. 6,062,746 and Szajewski, et al., U.S. Pat. No. 6,048,110, commonly assigned, which are incorporated herein by reference. The use of an apparatus whereby the processor can be used to write information onto the element, information which can be used to adjust processing, scanning, and image display is also envisaged. This system is disclosed in now allowed Stoebe, et al., U.S. patent applications Ser. No. 09/206,914 filed Dec. 7, 1998 and Ser. No. 09/333,092 filed Jun, 15, 1999, which are incorporated herein by reference.

Thermal processing is preferably carried out under ambient conditions of pressure and humidity. Conditions outside of normal atmospheric pressure and humidity are useful.

The components of the photothermographic element can be in any location in the element that provides the desired image. If desired, one or more of the components can be in one or more layers of the element. For example, in some cases, it is desirable to include certain percentages of the reducing agent, toner, stabilizer and/or other addenda in the overcoat layer over the photothermographic image recording layer of the element. This, in some cases, reduces migration of certain addenda in the layers of the element.

In view of advances in the art of scanning technologies, it has now become natural and practical for photothermographic color films such as disclosed in EP 0762 201 to be scanned, which can be accomplished without the necessity of removing the silver or silver-halide from the negative, although special arrangements for such scanning can be made to improve its quality. See, for example, Simmons U.S. Pat. No. 5,391,443.

Nevertheless, the retained silver halide can scatter light, decrease sharpness and raise the overall density of the film thus leading to impaired scanning. Further, retained silver halide can printout to ambient/viewing/scanning light, render non-imagewise density, degrade signal-to noise of the original scene, and raise density even higher. Finally, the retained silver halide and organic silver salt can remain in reactive association with the other film chemistry, making the film unsuitable as an archival media. Removal or stabilization of these silver sources are necessary to render the PTG film to an archival state.

Furthermore, the silver coated in the PTG film (silver halide, silver donor, and metallic silver) is unnecessary to the dye image produced, and this silver is valuable and the desire is to recover it is high.

Thus, it may be desirable to remove, in subsequent processing steps, one or more of the silver containing components of the film: the silver halide, one or more silver donors, the silver-containing thermal fog inhibitor if present, and/or the silver metal. The three main sources are the developed metallic silver, the silver halide, and the silver donor. Alternately, it may be desirable to stabilize the silver halide in the photothermographic film. Silver can be wholly or partially stabilized/removed based on the total quantity of silver and/or the source of silver in the film.

The removal of the silver halide and silver donor can be accomplished with a common fixing chemical as known in the photographic arts. Specific examples of useful chemicals include: thioethers, thioureas, thiols, thiones, thionamides, amines, quaternary amine salts, ureas, thiosulfates, thiocyanates, bisulfites, amine oxides, iminodiethanol-sulfur dioxide addition complexex, amphoteric amines, bis-sulfonylmethanes, and the carbocyclic and heterocyclic derivatives of these compounds. These chemicals have the ability to form a soluble complex with silver ion and transport the silver out of the film into a receiving vehicle. The receiving vehicle can be another coated layer (laminate) or a conventional liquid processing bath.

The stabilization of the silver halide and silver donor can also be accomplished with a common stabilization chemical. The previously mentioned silver salt removal compounds can be employed in this regard. With stabilization, the silver is not necessarily removed from the film, although the fixing agent and stabilization agents could very well be a single chemical. The physical state of the stabilized silver is no longer in large (>50 nm) particles as it was for the silver halide and silver donor, so the stabilized state is also advantaged in that light scatter and overall density is lower, rendering the image more suitable for scanning.

The removal of the metallic silver is more difficult than removal of the silver halide and silver donor. In general, two reaction steps are involved. The first step is to bleach the metallic silver to silver ion. The second step may be identical to the removal/stabilization step(s) described for silver halide and silver donor above. Metallic silver is a stable state that does not compromise the archival stability of the PTG film. Therefore, if stabilization of the PTG film is favored over removal of silver, the bleach step can be skipped and the metallic silver left in the film. In cases where the metallic silver is removed, the bleach and fix steps can be done together (called a blix) or sequentially (bleach+fix).

The process could involve one or more of the scenarios or permutaions of steps. The steps can be done one right after another or can be delayed with respect to time and location. For instance, heat development and scanning can be done in a remote kiosk, then bleaching and fixing accomplished several days later at a retail photofinishing lab. In one embodiment, multiple scanning of images is accomplished. For example, an initial scan may be done for soft display or a lower cost hard display of the image after heat processing, then a higher quality or a higher cost secondary scan after stabilization is accomplished for archiving and printing, optionally based on a selection from the initial display.

For illustrative purposes, a non-exhaustive list of photothermographic film processes involving a common dry heat development step are as follows:

1. heat development=>scan=>stabilize (for example, with a laminate)=>scan=>obtain returnable archival film.
2. heat development=>fix bath=>water wash=>dry=>scan=>obtain returnable archival film
3. heat development=>scan=>blix bath=>dry=>scan=>recycle all or part of the silver in film
4. heat development=>bleach laminate=>fix laminate=>scan=>(recycle all or part of the silver in film)
5. heat development=>scan=>blix bath=>wash=>fix bath=>wash=>dry=>obtain returnable archival film
6. heat development=>relatively rapid, low quality scan
7. heat development=>bleach=>wash=>fix=>wash=>dry=>relatively slow, high quality scan Photothermographic or photographic elements of the present invention can also be subjected to low volume processing ("substantially dry" or "apparently dry") which is defined as phototographic processing where the volume of applied developer solution is between about 0.1 to about 10 times, preferably about 0.5 to about 10 times, the volume of solution required to swell the photographic element. This processing may take place by a combination of solution application, external layer lamination, and heating. The low volume processing system may contain any of the elements described above for photothermographic systems. In addition, it is specifically contemplated that any components described in the preceding sections that are not necessary for the formation or stability of latent image in the origination film element can be removed from the film element altogether and contacted at any time after exposure for the purpose of carrying out photographic processing, using the methods described below.

An apparently dry photothermographic element or photographic element may receive some or all of the following three treatments:

(I) Application of a solution directly to the film by any means, including spray, inkjet, coating, gravure process and the like.

(II) Soaking of the film in a reservoir containing a processing solution. This process may also take the form of dipping or passing an element through a small cartridge.

(III) Lamination of an auxiliary processing element to the imaging element. The laminate may have the purpose of providing processing chemistry, removing spent chemistry, or transferring image information from the latent image recording film element. The transferred image may result from a dye, dye precursor, or silver containing compound being transferred in a image-wise manner to the auxiliary processing element. Heating of a photothermographic element during processing may be effected by any convenient means, including a simple hot plate, iron, roller, heated drum, microwave heating means, heated air, vapor, or the like. Heating may be accomplished before, during, after, or throughout any of the preceding treatments I–III. Heating may cause processing temperatures ranging from room temperature to 100° C. or above.

Once yellow, magenta, and cyan dye image records (or the like) have been formed in the processed photographic elements of the invention, conventional techniques can be employed for retrieving the image information for each color record and manipulating the record for subsequent creation of a color balanced viewable image. For example, it is possible to scan the photothermographic element successively within the blue, green, and red regions of the spectrum or to incorporate blue, green, and red light within a single scanning beam that is divided and passed through blue, green, and red filters to form separate scanning beams for each color record. A simple technique is to scan the photothermographic element point-by-point along a series of laterally offset parallel scan paths. The intensity of light passing through the element at a scanning point is noted by a sensor which converts radiation received into an electrical signal. Most generally this electronic signal is further manipulated to form a useful electronic record of the image. For example, the electrical signal can be passed through an analog-to-digital converter and sent to a digital computer together with location information required for pixel (point) location within the image. In another embodiment, this electronic signal is encoded with calorimetric or tonal information to form an electronic record that is suitable to allow reconstruction of the image into viewable forms such as computer monitor displayed images, television images, printed images, and so forth.

It is contemplated that many of imaging elements of this invention will be scanned prior to the removal of silver halide from the element. The remaining silver halide yields a turbid coating, and it is found that improved scanned image quality for such a system can be obtained by the use of scanners that employ diffuse illumination optics. Any technique known in the art for producing diffuse illumination can be used. Preferred systems include reflective systems, that employ a diffusing cavity whose interior walls are specifically designed to produce a high degree of diffuse reflection, and transmissive systems, where diffusion of a beam of specular light is accomplished by the use of an optical element placed in the beam that serves to scatter light. Such elements can be either glass or plastic that either incorporate a component that produces the desired scattering, or have been given a surface treatment to promote the desired scattering.

One of the challenges encountered in producing images from information extracted by scanning is that the number of pixels of information available for viewing is only a fraction of that available from a comparable classical photographic print. It is, therefore, even more important in scan imaging to maximize the quality of the image information available. Enhancing image sharpness and minimizing the impact of aberrant pixel signals (i.e., noise) are common approaches to enhancing image quality. A conventional technique for minimizing the impact of aberrant pixel signals is to adjust each pixel density reading to a weighted average value by factoring in readings from adjacent pixels, closer adjacent pixels being weighted more heavily.

The elements of the invention can have density calibration patches derived from one or more patch areas on a portion of unexposed photographic recording material that was subjected to reference exposures, as described by Wheeler et al U.S. Pat. No. 5,649,260, Koeng at al U.S. Pat. No. 5,563,717, and by Cosgrove et al U.S. Pat. No. 5,644,647.

Illustrative systems of scan signal manipulation, including techniques for maximizing the quality of image records, are disclosed by Bayer U.S. Pat. No. 4,553,156; Urabe et al U.S. Pat. No. 4,591,923; Sasaki et al U.S. Pat. No. 4,631,578; Alkofer U.S. Pat. No. 4,654,722; Yamada et al U.S. Pat. No. 4,670,793; Klees U.S. Pat. Nos. 4,694,342 and 4,962,542; Powell U.S. Pat. No. 4,805,031; Mayne et al U.S. Pat. No. 4,829,370; Abdulwahab U.S. Pat. No. 4,839,721; Matsunawa et al U.S. Pat. Nos. 4,841,361 and 4,937,662; Mizukoshi et al U.S. Pat. No. 4,891,713; Petilli U.S. Pat. No. 4,912,569; Sullivan et al U.S. Pat. Nos. 4,920,501 and 5,070,413; Kimoto et al U.S. Pat. No. 4,929,979; Hirosawa et al U.S. Pat. No. 4,972,256; Kaplan U.S. Pat. No. 4,977,521; Sakai U.S. Pat. No. 4,979,027; Ng U.S. Pat. No. 5,003,494; Katayama et al U.S. Pat. No. 5,008,950; Kimura et al U.S. Pat. No. 5,065,255; Osamu et al U.S. Pat. No. 5,051,842; Lee et al U.S. Pat. No. 5,012,333; Bowers et al U.S. Pat. No. 5,107,346; Telle U.S. Pat. No. 5,105,266; MacDonald et al U.S. Pat. No. 5,105,469; and Kwon et al U.S. Pat. No. 5,081,692. Techniques for color balance adjustments during scanning are disclosed by Moore et al U.S. Pat. No. 5,049,984 and Davis U.S. Pat. No. 5,541,645.

The digital color records once acquired are in most instances adjusted to produce a pleasingly color balanced image for viewing and to preserve the color fidelity of the image bearing signals through various transformations or renderings for outputting, either on a video monitor or when printed as a conventional color print. Preferred techniques for transforming image bearing signals after scanning are disclosed by Giorgianni et al U.S. Pat. No. 5,267,030, the disclosures of which are herein incorporated by reference. Further illustrations of the capability of those skilled in the art to manage color digital image information are provided by Giorgianni and Madden *Digital Color Management*, Addison-Wesley, 1998.

EXAMPLE 1

The following examples illustrate the synthesis of some blocked developers that are useful in the invention.

Preparation of D-2

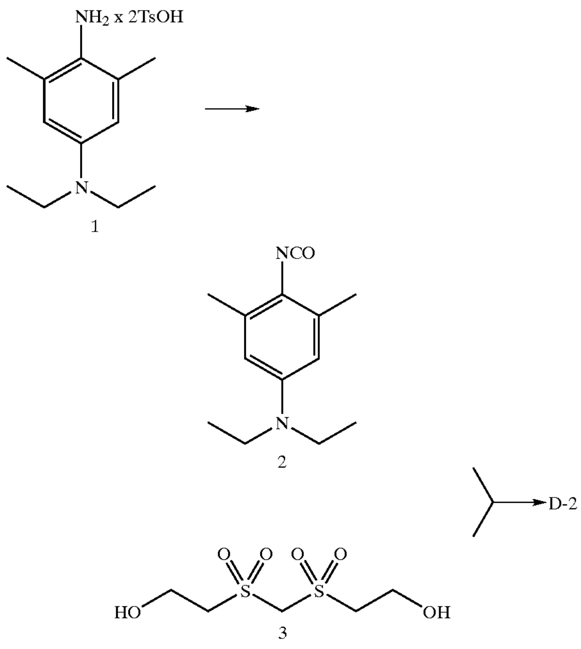

1

2

3

D-2

Preparation of 2

Water (450 mL) was slowly added at 0° C. to a mixture of 2,6-dimethyl-4-(N,N-diethyl)aniline ditosylate (1) (268.4 g, 0.50 mol), potassium bicarbonate (500.6 g, 5.00 mol) and dichloromethane (900 mL), followed by a 1.9M toluene solution of phosgene (550 mL, 1.00 mol) at 4–7° C. over a period of 30 min. Following the addition, the mixture was stirred cold for 30 min and diluted with dichloromethane (750 mL) and water (1000 mL). The layers were separated and the aqueous one extracted with dichloromethane (350 mL). Combined organic solutions were dried over sodium sulfate and the solvents were distilled off in vacuo at 45° C. The crude product was dissolved in ligroin (700 mL), the solution treated with charcoal, filtered through SuperCel and concentrated in vacuo at 50° C., giving 111.0 g (0.50 mol, 100%) of isocyanate 2 as a yellow oil. $^1H$ NMR ($CDCl_3$): δ 6.35 (s, 2H), 3.30 (q, 4H), 2.25 (s, 6H), 1.15 (t, 6H).

Preparation of D-2

A solution of isocyanate 2 (177.6 g, 0.81 mol), diol 3 (87.1 g, 0.375 mol) and dibutyltin diacetate (1 mL) in 900 mL of acetonitrile was stirred at 50° C. under nitrogen for 3 days. The mixture was cooled to room temperature, filtered and the filtrate taken to dryness. The crystalline residue was stirred with isopropyl ether (500 mL), the product collected by filtration, washed with isopropyl ether (2×250 mL) and then ethanol (2×250 mL). Yield 220.9 g (0.33 mol, 88%), m.p.173–175° C.

Preparation of D-3, D-4 and D-9

Blocked developers D-3, D-4 and D-9 were prepared as described above for D-2 from isocyanate 2 and appropriate alcohols in the presence of catalytic amounts of dibutyltin diacetate. The yields and melting points are listed below in Table 1 below.

TABLE 1

| Developer | Yield (%) | m.p.(° C.) |
|---|---|---|
| D-3 | | 161–163 |
| D-4 | 84 | 91–93 |
| D-9 | 79 | 110–114 |

EXAMPLE 2

A hardened silver halide color photothermographic element is prepared having:

(A) a red-light-sensitive silver halide layer unit with 2.37 $g/m^2$ of silver behenate, 0.43 $g/m^2$ of coupler A-1, and a blocked developer which liberates 0.2 g of 4-N,N-diethyl-2,6-dimethylphenlyenediamine on heating, all in 4.74 $g/m^2$ of gelatin;

(B) a green-light-sensitive layer unit with 2.37 $g/m^2$ of silver behenate, 0.43 $g/m^2$ of coupler A-1, and a blocked developer which liberates 0.2 g of 4-(N-ethyl-N-2-hydroxyethyl)-2-methylphenylenediamine on heating, all in 4.74 $g/m^2$ of gelatin; and (C) a blue-light-sensitive layer unit with 2.37 $g/m^2$ of silver behenate, 0.43 $g/m^2$ of coupler A-1, a a blocked developer which liberates 0.2 g of 2-hyrazinobenzothiazole on heating, all in 4.74 $g/m^2$ of gelatin.

The element further consists of a protective overcoat and conventional components as known in the art. The photographic element is imagewise exposed to white light and thermally developed. A red density of 1.46, a green density of 1.92 and a blue density of 1.85 is formed. The formed deposits have excellent stability and fastness.

The invention has been described in detail with particular reference to certain preferred embodiments thereof, but it will be understood that variations and modifications can be effected within the spirit and scope of the invention.

What is claimed is:

1. A compound useful as a blocked developer having the following structure:

$$DEV—(LINK\ 1)_l—(TIME)_m—(LINK\ 2)_n—B \qquad I$$

wherein,

DEV is a silver-halide color developing agent;

LINK 1 and LINK 2 are linking groups;

TIME is a timing group;

1 is 0 or 1;

m is 0, 1, or 2;

n is 0 or 1;

1+n is 1 or 2;

B is a blocking group or B is:

$$—B'—(LINK\ 2)_n—(TIME)_m—(LINK\ ^1)_l—DEV$$

wherein B' also blocks a second developing agent DEV; wherein the blocked developer liberates a developing agent within the following structure:

$$A—(CR^1{=}CR^2)_n—NHY$$

wherein:

n is 0, 1 or 2;

A is OH, or $NR^3R^4$;

Y is H, or a group that cleaves before or during a coupling reaction to form YH; and $R^1$ $R^2$, $R^3$ and $R^4$, which can be the same or different are individually H, alkyl, substituted alkyl, alkenyl, substituted alkenyl, aryl, substituted aryl, halogen, cyano, alkoxy, substituted alkoxy, aryloxy, substituted aryloxy, amino, substituted amino, alkylcarbonamido, substituted alkylcarbonamido, arylcarbonamido, substituted arylcarbonamido, alkylsulfonamido, arylsulfonamido, substituted alkylsulfonamido, substituted arylsulfonamido, or sulfamyl or wherein at least two of $R^1$ $R^2$, $R^3$ and $R^4$ together can further form a substituted or unsubstituted carbocyclic or heterocyclic ring structure, wherein the blocked developer according to the present invention enables the formation of a cyan colored dye when the oxidized form of the released developer reacts with a coupler having the following structure:

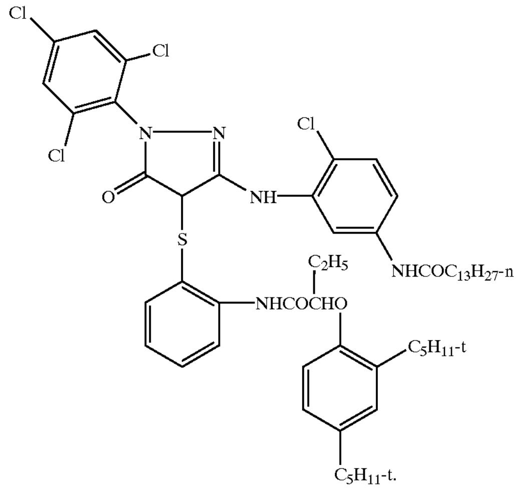

2. A compound useful as a blocked developer having the following structure:

$$DEV—(LINK\ 1)_l—(TIME)_m—(LINK\ 2)_n—B \qquad I$$

wherein,

DEV is a silver-halide color developing agent;

LINK 1 and LINK 2 are linking groups;

TIME is a timing group;

1 is 0 or 1;

m is 0, 1,or 2;

n is 0 or 1;

1+n is 1 or 2;

B is a blocking group or B is:

$$—B'—LINK\ 2)_n—(TIME)_m—(LINK\ 1)_l—DEV$$

wherein B' also blocks a second developing agent DEV; wherein the blocked developer liberates a developing agent within the following structure:

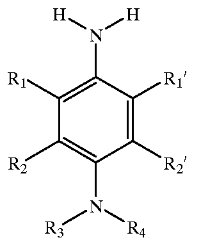

wherein $R_1$, $R_1$', $R_2$, $R_2$', $R_3$ and $R_4$ which can be the same or different are individually H, alkyl, substituted alkyl, alkenyl, substituted alkenyl, aryl, substituted aryl, halogen, cyano, hydroxy, alkoxy, substituted alkoxy, aryloxy, substituted aryloxy, amino, substituted amino, alkylcarbonamido, substituted alkylcarbonamido, arylcarbonamido, substituted arylcarbonamido, alkylsulfonamido, arylsulfonamido, substituted alkylsulfonamido, substituted arylsulfonamido, or sulfamyl or wherein at least two of $R_1$, $R_1$', $R_2$, $R_2$', $R_3$ and $R_4$ together further form a substituted or unsubstituted carbocyclic or heterocyclic ring structure; except that neither $R_1$ nor $R_1$' can be H.

3. The compound of claim 2, wherein the blocked developer liberates a developer represented by the following structure.

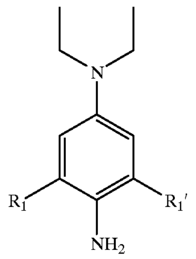

wherein $R_1$ and $R_1$' are as described above.

4. A compound useful as a blocked developer according to claim 1, wherein the developer is selected from the group consisting of 4-N, N-diethyl-2-methyl-6-methoxyphenylenediamine, 4-N, N-diethyl-2,6-dimethylphenylenediamine, 4-(N-ethyl-N-2-methanesulfonylaminoethyl)-2,6-dimethylphenylenediamine, 4-(N-ethyl-N-2-hydroxyethyl)-2,6-dimethylphenylenediamine, 4-N,N-diethyl-2-methanesulfonylaminoethyl-6-methylphenylenediamine, 4-(N-ethyl-N-2-hydroxyethyl)-2-ethoxyphenylenediamine, and 4-(N-ethyl-N-2-methoxyethyl)-2,6-dimethylphenylenediamine.

5. A compound useful as a blocked developer according to claim 1, wherein the developer has an $E_{1/2}$ at pH 11 less positive than 200 mV.

6. A compound useful as a blocked developer according to claim 4, wherein the developer has the following structure:

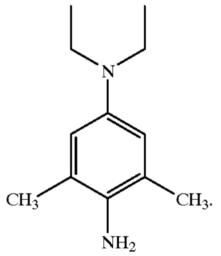

* * * * *